United States Patent [19]
Hofmann

[11] Patent Number: 6,120,493
[45] Date of Patent: Sep. 19, 2000

[54] METHOD FOR THE INTRODUCTION OF THERAPEUTIC AGENTS UTILIZING AN ELECTROPORATION APPARATUS

[75] Inventor: Gunter A. Hofmann, San Diego, Calif.

[73] Assignee: Genetronics, Inc., San Diego, D.C.

[21] Appl. No.: 09/206,635

[22] Filed: Dec. 7, 1998

Related U.S. Application Data

[63] Continuation-in-part of application No. 09/014,291, Jan. 27, 1998.

[51] Int. Cl.[7] .................................................... A61M 31/00
[52] U.S. Cl. .............................. 604/506; 604/21; 607/148
[58] Field of Search ................................ 604/21, 20, 506; 607/108, 116, 143, 148; 435/173.6

[56] References Cited

U.S. PATENT DOCUMENTS 5,344,440  9/1994  Stephen .
5,674,267 10/1997  Mir et al. .
6,009,347 12/1999  Hofmann .

*Primary Examiner*—Mark Bockelman
*Attorney, Agent, or Firm*—Gray Cary Ware & Freidenrich LLP; Lisa A. Haile

[57] ABSTRACT

A method is provided for the introduction of an agent to a neoplastic cell for electroporating the cell, including contacting the cell with an electrode template apparatus. The electrode template apparatus is utilized to apply an electric field to the cell in order to introduce the agent into the cell. A method is also provided for the introduction of an agent to a tissue for electroporating a cell in the tissue, including contacting the tissue with an electrode template apparatus. The tissue is contacted with the agent and a pulse of high amplitude electric signals is applied to the cell utilizing the apparatus, for electroporation of the cell with the agent.

30 Claims, 17 Drawing Sheets

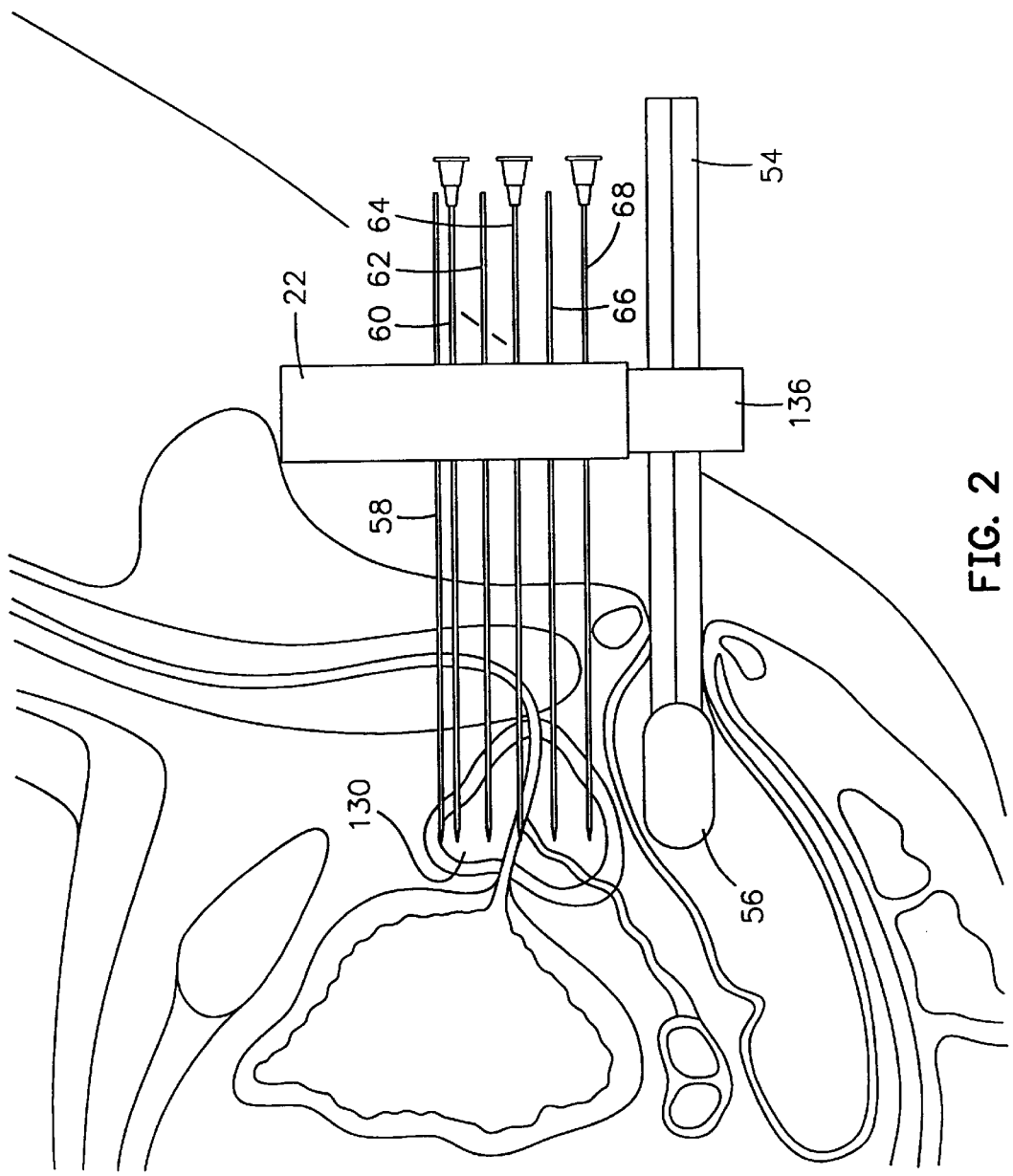

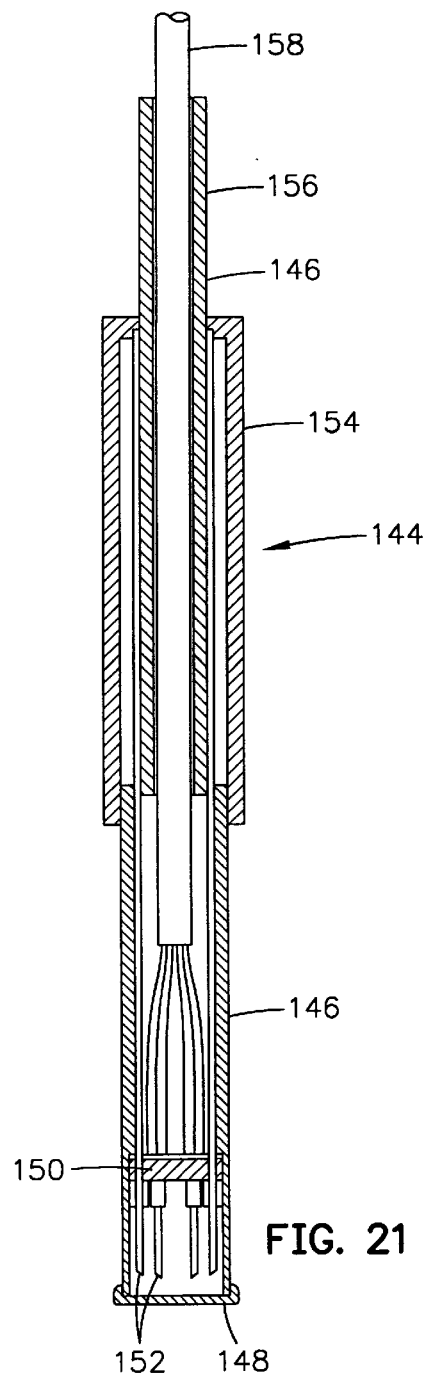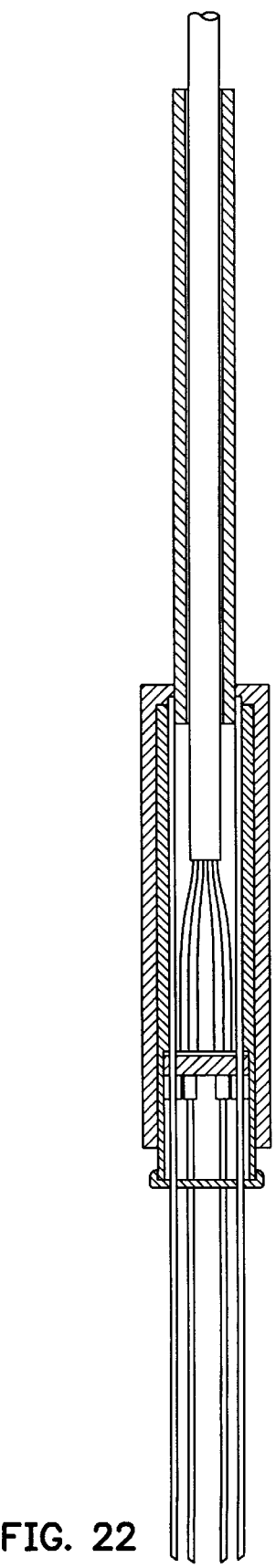
FIG. 21
FIG. 22

METHOD FOR THE INTRODUCTION OF THERAPEUTIC AGENTS UTILIZING AN ELECTROPORATION APPARATUS

CROSS REFERENCE TO RELATED APPLICATION

This application is a continuation-in-part of U.S. patent application Ser. No. 09/014,291, filed Jan. 27, 1998, herein incorporated by reference.

FIELD OF THE INVENTION

This invention relates generally to the field of electroporation, and more specifically to the use of electroporation to introduce agents to a neoplastic cell to damage the cell.

BACKGROUND OF THE INVENTION

A cell has a natural resistance to the passage of molecules through its membranes into the cell cytoplasm. Scientists in the 1970's first discovered "electroporation", where electrical fields are used to create pores in cells without causing permanent damage to them. This discovery made possible the insertion of large molecules directly into cell cytoplasm. Electroporation was further developed to aid in the insertion of various molecules into cell cytoplasm by temporarily creating pores in the cells through which the molecules pass into the cell.

Electroporation has been used to implant materials into many different types of cells. Such cells, for example, include eggs, platelets, human cells, red blood cells, mammalian cells, plant protoplasts, plant pollen, liposomes, bacteria, fungi, yeast, and sperm. Furthermore, electroporation has been used to implant a variety of different materials, referred to herein as "implant materials", "implant molecules", and "implant agents". These materials have included DNA, genes, and various chemical agents.

Electroporation has been used in both in vitro and in vivo procedures to introduce foreign material into living cells. With in vitro applications, a sample of live cells is first mixed with the implant agent and placed between electrodes such as parallel plates. Then, the electrodes apply an electrical field to the cell/implant mixture.

With in vivo applications of electroporation, electrodes are provided in various configurations such as, for example, a caliper that grips the epidermis overlying a region of cells to be treated. Alternatively, needle-shaped electrodes may be inserted into the patient, to access more deeply located cells. In either case, after the implant agent is injected into the treatment region, the electrodes apply an electrical field to the region. Examples of systems that perform in vivo electroporation include the Electro Cell Manipulator ECM 600 product, and the Electro Square Porator T820, both made by and available from the BTX Division of Genetronics, Inc.

In the treatment of certain types of cancer with chemotherapeutic agents it is necessary to use a high enough dose of a drug to kill the cancer cells without killing an unacceptably high number of normal cells. If the chemotherapy drug could be inserted directly inside the cancer cells, this objective could be achieved. Some of the best anti-cancer drugs, for example, bleomycin, normally cannot penetrate the membranes of certain cancer cells effectively. However, electroporation makes it possible to insert the bleomycin into the cells.

In general, the treatment is carried out by infusing an anticancer drug directly into the tumor and applying an electric field to the tumor between one or more pairs of electrodes. The molecules of the drug are suspended in the interstitial fluid between and in and around the tumor cells. By electroporating the tumor cells, molecules of the drug adjacent to many of the cells are forced or drawn into the cell, subsequently killing the cancerous tumor cell. "Electrochemotherapy" is the therapeutic application of electroporation to deliver chemotherapeutic agents directly to tumor cells.

Known electroporation techniques (both in vitro and in vivo) function by applying a brief high voltage pulse to electrodes positioned around the treatment region. The electric field generated between the electrodes causes the cell membranes to temporarily become porous, whereupon molecules of the implant agent enter the cells. In known electroporation applications, this electric field comprises a single square wave pulse on the order of 1000 V/cm, of about 100 $\mu$s duration. Such a pulse may be generated, for example, in known applications of the Electro Square Porator T820, made by the BTX Division of Genetronics, Inc. Needle electrodes have been found to be very useful in the application of electroporation to many organs of the body and to tumors in the body.

An electric field may actually damage the electroporated cells in some cases. For example, an excessive electric field may damage the cells by creating permanent pores in the cell walls. In extreme cases, the electric field may completely destroy the cell. It is desirable that improved electroporation methods and apparatus with selectable needle electrode arrays be available.

SUMMARY OF THE INVENTION

The invention provides a therapeutic method utilizing an electroporation apparatus for the treatment of cells, particularly a neoplastic cell, in order to damage the cell.

A method is provided for the introduction of an agent to a neoplastic cell for damaging the cell, including contacting the cell with an electrode template apparatus. The electrode template apparatus includes a primary support member having opposite surfaces, a plurality of bores extending through the support member and through the opposite surfaces, a plurality of conductors on the support member separately connected to at least one of the plurality of bores, a plurality of electrodes selectively insertable in the plurality of bores so that each conductor is connected to at least one electrode, and a means for connecting the conductors to a power supply. The electrode template apparatus is utilized to apply a high voltage electric field to the cell in order to introduce the agent into the cell.

A method is provided for the introduction of an agent to a tissue for damaging a cell in the tissue, including contacting the tissue with an electrode template apparatus. The apparatus includes a primary support member having opposite parallel surfaces, a plurality of bores arranged in a rectangular array and extending through the support member and through the opposite surfaces, a plurality of conductors on the support member separately connected to at least one of the plurality of bores, a plurality of needle electrodes mounted in the plurality of bores so that each conductor is connected to at least one electrode, wherein at least one of the needle electrodes has a tubular configuration for injection of the agent into the tissue; and a means for connecting the conductors to a power supply. The tissue is contacted with the agent; and a pulse of high amplitude electric signals is applied to the cell, for electroporation of the cell with the agent.

BRIEF DESCRIPTION OF THE DRAWINGS

FIG. 2 is a side elevation view showing the embodiment of FIG. 1 in use.

FIG. 13 is a schematic illustration of needle electrode arrays.

FIG. 21 is a side elevation view illustrating another embodiment of the invention showing the needle electrodes mounted in a holder with the electrodes in the retracted position.

FIG. 22 is a view like FIG. 16 showing the needle electrodes in the extended position.

DESCRIPTION OF THE PREFERRED EMBODIMENTS

Figures 1, 2A:
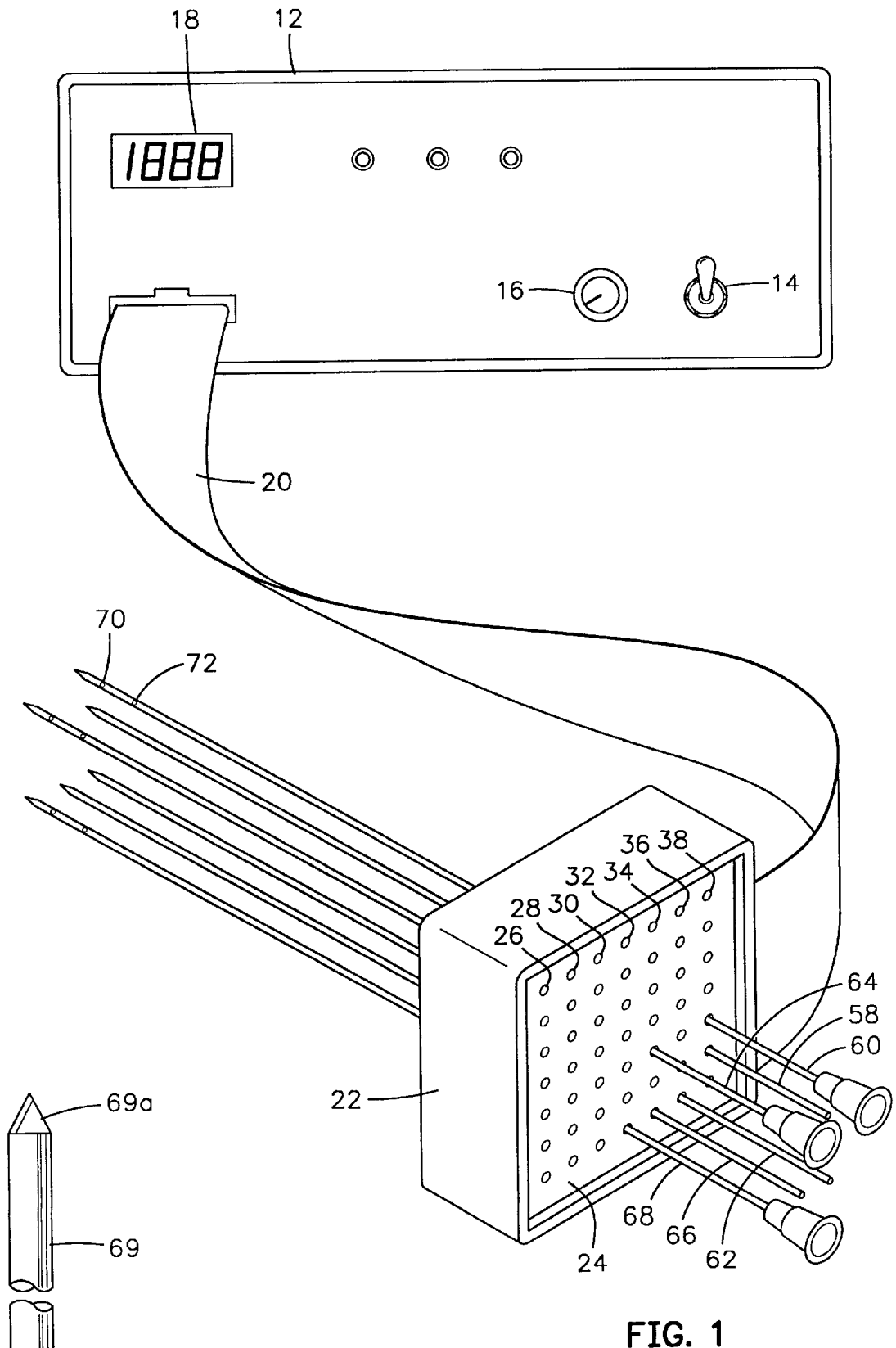
FIG. 1 is a perspective view illustrating a system employing an exemplary embodiment of the present invention.
FIG. 2A is an enlarged partial side elevation view illustrating details of one embodiment of a needle electrode tip.

It must be noted that as used herein and in the appended claims, the singular forms "a", "and", and "the" include plural referents unless the context clearly dictates otherwise. Thus, for example, reference to "a cell" includes at least one and including a plurality of such cells and reference to "the needle" includes reference to one or more needles and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cells, therapeutic agents, and methodologies which are described in the publications which might be used in connection with the presently described invention. The publications discussed above and throughout the text are provided solely for their disclosure prior to the filing date of the present application.

The invention provides a method of using an apparatus for the therapeutic application of electroporation. The method includes infusion of a chemotherapeutic agent or molecule and electroporation of the agent or molecule into a tumor. The agent is injected into tissue, and at least one voltage pulse is applied between needle electrodes disposed in tissue, wherein the needles function as the electrodes, thereby generating electric fields in cells of the tissue. The needle electrode assemblies described below enable the in vivo positioning of electrodes in or adjacent to subsurface tumors or other tissue. Such therapeutic treatment is called electroporation therapy (EPT), a form of electrochemotherapy. While the focus of the description below is EPT, the invention may be applied to other treatments, such as gene therapy of certain organs of the body.

THERAPEUTIC METHOD

The therapeutic method of the invention includes electrotherapy, also referred to herein as electroporation therapy (EPT), using the apparatus of the invention for the delivery of an agent to a cell or tissue, either in vivo or in vitro. The term "agent" or "molecule" as used herein refers to drugs (e.g., chemotherapeutic agents), nucleic acids (e.g., polynucleotides), peptides and polypeptides, including antibodies. The term polynucleotides include DNA, cDNA and RNA sequences.

A "chemotherapeutic agent" is an agent having an antitumor or cytotoxic effect. Such agents can be "exogenous" agents, which are not normally found in the organism (e.g., chemical compounds and drugs). Such drugs or agents include bleomycin, neocarcinostatin, suramin, doxorubicin, taxol, mitomycin C and cisplatin. Other exogenous chemotherapeutic agents will be known to those of skill in the art (see for example The Merck Index). Chemotherapeutic agents can also be "endogenous" agents, which are native to the organism. Endogenous agents include suitable naturally-occurring agents, such as biological response modifiers such as cytokines, or hormones.

Therapeutic peptides or polypeptides may also be included in the therapeutic method of the invention. For example, immunomodulatory agents and other biological response modifiers can be administered for incorporation by a cell. The term "biological response modifiers" is meant to encompass substances which are involved in modifying the immune response. Examples of immune response modifiers include such compounds as cytokines. The term "cytokine" is used as a generic name for a diverse group of soluble proteins and peptides which act as humoral regulators at nano- to picomolar concentrations and which, either under normal or pathological conditions, modulate the functional activities of individual cells and tissues. Also included are polynucleotides which encode metabolic enzymes and proteins, including antiangiogenesis compounds, e.g., Factor VIII or Factor IX.

In electrochemotherapy, electroporation is used to deliver chemotherapeutic agents directly into tumor cells. "Electroporation" refers to increased permeability of a cell membrane and/or a portion of cells of a targeted tissue (or population of cells) to an agent, when the increased permeability occurs as a result of an application of voltage across a cell. It is believed that electroporation facilitates entry of a chemotherapeutic agent such as bleomycin or other drugs into the tumor cell by creating pores in the cell membrane. Treatment is carried out by administering an anticancer drug directly into the tumor and applying an electric field to the tumor between a pair of electrodes. Without being bound by theory, the molecules of the drug are suspended in the interstitial fluid between and in and around the tumor cells. By electroporating the tumor cells, molecules of the drug adjacent to many of the cells are forced or drawn into the cell, subsequently killing the cancerous tumor cell.

Any cell in vivo can be treated by the method of the invention. The method of the invention is useful in treating cell proliferative disorders of the various organ systems of the body. The method of the invention for the treatment of cells, including but not limited to the cells of the prostate, pancreas, larynx, pharynx, lip, throat, lung, kidney, muscle, breast, colon, uterus, thymus, testis, skin, and ovary. The cells may be cells from any mammal, including mice, rats, rabbits, dogs, cats, pigs, cows, sheep, and humans. In a preferred embodiment, the cells are human cells.

The term "neoplasia" refers to a disease of inappropriate cell proliferation. This derangement is most evident clinically when tumor tissue bulk compromises the function of vital organs. The term "cell proliferative disorder" denotes malignant as well as non-malignant cell populations which often appear to differ from the surrounding tissue both morphologically and genotypically. Malignant cells (i.e., tumors or cancer) develop as a result of a multi-step process. Concepts describing normal tissue growth are applicable to malignant tissue because normal and malignant tissues can share similar growth characteristics, both at the level of the single cell and at the level of the tissue. Tumors are as much a disease of disordered tissue growth regulation as of disordered cellular growth regulation. The growth characteristics of tumors are such that new cell production exceeds cell death; a neoplastic event tends to produce an increase in the proportion of stem cells undergoing self-renewal and a corresponding decrease in the proportion progressing to maturation (McCulloch, E. A., et al., "The contribution of blast cell properties to outcome variation in acute myeloblastic leukemia (AML), *Blood* 59:601–608, 1982). In one embodiment, the cells treated by the method of the invention are neoplastic cells. Thus, the electroporation methods of the invention can be used to treat cell proliferative disorders.

A number of experiments have been conducted to test therapeutic application of electroporation for cell proliferative disorders in a process termed electrochemotherapy. This treatment is carried out by infusing an anticancer drug directly into the tumor and applying an electric field to the tumor between a pair of electrodes. The field strength must be adjusted reasonably accurately so that electroporation of the cells of the tumor occurs without damaging significant numbers of normal or healthy cells. This can be carried out with external tumors by applying the electrodes to opposite sides of the tumor so that the electric field is between the electrodes. The distance between the electrodes can then be measured and a suitable voltage according to the formula $E=V/d$ can then be applied to the electrodes. The electrode apparatus of use with the methods of the invention has electrodes that can be inserted into or adjacent to tumors so that predetermined electric fields can be generated in the tumor tissue for electroporation of the cells of the tumor. In one embodiment, the electric field applied by the apparatus is from about 50 V/cm to 1500 V/cm. The electrical field can be applied as from about 1 to about 10 electrical pulses. In one embodiment, the electrical pulse is delivered as a pulse lasting from about 5 $\mu$sec to 50 msec in duration. The electrical pulse can be applied as a square wave pulse, an exponential wave pulse, a unipolar oscillating wave form of limited duration, or a bipolar oscillating wave form of limited duration. In one embodiment, the electrical pulse is comprised of a square wave pulse.

The electrical pulse can be delivered before, at the same time as, or after, the application of the agent. The chemical composition of the agent will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Further, such drugs as bleomycin, which have a very negative log P, (P being the partition coefficient between octanol and water), are very large in size (MW=1400), and are hydrophilic, thereby associating closely with the lipid membrane, diffuse very slowly into a tumor cell and are typically administered prior to or substantially simultaneous with the electric pulse. Preferably, the molecule is administered substantially contemporaneously with the electroporation treatment. The term "substantially contemporaneously" means that the molecule and the electroporation treatment are administered reasonably close together with respect to time. The administration of the molecule or therapeutic agent and electroporation can occur at any interval, depending upon such factors, for example, as the nature of the tumor, the condition of the patient, the size and chemical characteristics of the molecule and half-life of the molecule.

Electroporation can help minimize the amount of a chemotherapeutic agent used, these chemicals frequently being harmful to normal cells. In particular, less of the chemotherapeutic agent can be introduced into the tumorous area because the electroporation will enable more of the implant agent to actually enter the cell.

"Administering" an agent in the methods of the invention may be accomplished by any means known to the skilled artisan. Administration of an agent in the methods of the invention can be, for example, parenterally by injection, rapid infusion, nasopharyngeal absorption, dermal absorption, and orally. In the case of a tumor, for example, a chemotherapeutic or other agent can be administered locally, systemically or directly injected into the tumor. In one embodiment, when a drug is administered directly into the tumor the drug is injected in a "fanning" manner. The term "fanning" refers to administering the drug by changing the direction of the needle as the drug is being injected or by multiple injections in multiple directions like opening up of a hand fan, rather than as a bolus, in order to provide a greater distribution of drug throughout the tumor. It is desirable to adjust the volume of the drug-containing solution to ensure adequate administration to the a tumor, in order to insure adequate distribution of the drug throughout the tumor. For example, a typical injection may based on the size, volume, or weight of the tissue being treated. In one specific, non-limiting example using dogs described herein (see EXAMPLES), 0.25 ml/cm$^3$ of drug-containing solution is injected into the treated tissue. Thus, the volume of drug containing solution is adjusted based on the size of the treated tissue. In the human tissues, the volume would similarly be adjusted to ensure adequate perfusion of the tumor. In one embodiment, injection is done very slowly all around the base of a tumor and by fanning in a human subject.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Besides the inert diluents, such compositions can also include adjuvants, wetting agents, emulsifying and suspending agents. Further, vasoconstrictor agents can be used to keep the therapeutic agent localized prior to pulsing.

ELECTROPORATION APPARATUS

Referring to FIG. 1 of the drawing, an electroporation system 10 embodying an exemplary embodiment useful in the methods of the present invention is illustrated. The system comprises a pulse generator 12 for generating high voltage pulses and is preferably of the type sold under the mark "MedPulser" by Genetronics, Inc. The pulse generator is preferably of the type disclosed in application Ser. No. 08/905,240, entitled, "Method of Treatment Using Electroporation Mediated Delivery of Drugs and Genes", filed Aug. 1, 1997 (herein incorporated by reference), wherein a user defined pulse may be selected and various parameters can be programmed. This enables pre-selectable pulsing schemes suitable for the particular applications.

The pulsing unit has the usual control panel with a power selector switch 14 and may also have other controls such as a remote activation means 16. The panel would also have various indicators to indicate to the operator various conditions and parameters, such as a digital readout 18 for therapy set-point. A conductor cable 20 connects the pulse generator to a connector and template 22 for a plurality of electrodes. The electrode connector and template 22 serves to connect selected electrodes to selected conductors, which in turn connect the electrodes to the pulse generator. The template also aids in establishing a pre-determined array or multiple arrays of electrodes.

A precise and controlled voltage must be applied to the tissue in order to provide the optimum electroporation or poration of the cells. Therefore, it is essential that the spacing of the electrodes be known so that the optimum voltage may be applied between the selected electrodes. The voltage must be applied in accordance with the spacing between the electrodes in order to apply the optimum voltage to the cells. The connector template 22 provides a means of selectively positioning any number of electrodes in a pre-determined array with pre-determined spacing.

The illustrated system was initially designed for using needle electrodes to apply electroporation therapy to prostate cancer. However, it will be appreciated that this system may be utilized for any number of external and internal tumors or organs of the body that can be reached from a body or other surface. For example, this system will enable the treatment of prostate tumors, breast tumors, local tumors, pancreatic tumors, liver tumors, or any other organ within the body that is accessible by needle electrodes or any other manner including open surgery. While the discussion herein has been primarily for the insertion of drugs into cells within tumors, or the like, it will also be appreciated that it can be used for the insertion of DNA or other genetic materials into cells within an organ or any selected tissue in the body for altering or generating a genetic response within an organ in the body, or within cells in that organ or tissue.

The applicant has found through experimentation that pulsing between opposed sets of multiple electrodes such as at least sets of pairs of electrodes in a multiple electrode array, preferably set up in parallel, rectangular or square patterns, provides improved results over that of pulsing between a pair of electrodes. Disclosed, for example, in application Ser. No. 08/467,566 entitled, "Electroporation Mediated Delivery of Drugs and Genes" is an array of needles wherein a plurality of pairs of needles define an area and may be pulsed during the therapeutic treatment. In that application, which is incorporated herein by reference as though fully set forth, needles were disposed in a circular array, but have connectors and switching apparatus enabling a pulsing between opposing pairs of needle electrodes.

The connector template of the present invention is designed to provide a system for accurately establishing a pre-selected array of needle electrodes, with a pre-determined spacing between the multiple electrodes, positioned within a tissue where electroporation is desired. The connector (22) is in the form of a support body having a plurality of rows of bores through which needle electrodes may be selectively inserted to define a selected array and connected via the through holes by conductors to the pulse generator by a suitable connector such as cable. In the illustrated embodiment, seven rows of seven bores are provided with the bores and rows spaced an equal distance apart. The spacing between the rows may be selected for the particular application, but an exemplary preferred spacing is on the order of about 0.65 cm. With this arrangement, each needle electrode can be spaced a distance of 0.65 cm from an adjacent electrode.

The electrodes are positioned in the grid in a selected manner to cover the desired areas of the tissue and the connections to the electrodes, such that the needles may be selectively distributed throughout the area of a tumor such that each square (bound by four needles or two pairs) within the tumor can be subjected to four pulses of alternate polarity rotating 90° between pulses. The switching may be done by electronic means square after square at a high frequency so that the total treatment time is on the order of a few seconds. With such an array, high voltages may be applied to the cells between the electrodes without subjecting other areas of tissue to uncomfortable voltage or current levels.

As shown in FIGS. 1 and 2, the exemplary connector template is a box-like support structure having a front face 24 and a back face (not shown). A first row of through bores 26, 28, 30, 32, 34, 36, and 38 are connected on the upper surface by means of conductors 40, 42, 44, 46, 48, 50, and 52 to a side edge of the support housing where they are connected by suitable means, either directly or by a plug and socket structure to the cable 20.

Second and subsequent rows of the through holes (not numbered) will be connected by conductors on the different levels of the laminate making up the connector structure as will be subsequently described. This enables a closer spacing of the electrodes. An exemplary group of needles 58, 60, 62, 64, 66 and 68 are shown in some of the bores. Certain of the electrodes 60, 64 and 68 are hollow and have a suitable connector at the outer end to enable the infusion of drugs or genes. These needles also have one or more suitable outlets such as an open end or one or more ports at or near the inserted end. For example, the hollow needle electrodes are shown to have outlet ports, with the ports of electrode 60 shown to have outlet ports identified by reference numerals 70 and 72.

Referring specifically to FIG. 2, the illustrated connector template is shown in use in treatment of a prostate cancer or the like. In this instance, the connector 22 is shown mounted on an elongated support rod 54 of an ultra-sound probe 56 which is shown inserted into the rectum of a patient. The sound probe is used to visualize the prostate and the location of the electrodes in the prostate. The template is then in a position such that a plurality of the needle electrodes 58, 60 and 62 are inserted through three of the horizontal through bores, as illustrated, and into the prostate of the patient. In this instance, two of the needle electrodes, 58 and 62, are illustrated as being solid needle electrodes and a center electrode 60 is shown to be hollow to enable the injection of molecules, such as a drug or a therapeutic agent or other material. A second group of needle electrodes 64, 66 and 68 are below the aforementioned electrodes and extend through the through bores of the connector template and into the prostate of the patient. In this instance, two of these needles 64 and 68 are hollow to enable the injection of a therapeutic or other agent into the prostate of the patient. These may be left in place following the injection of the therapeutic agent and serve as the electrodes for the application of the electrical pulses to the tissue of the prostate or cancer cells within the prostate. In one embodiment of the invention, the needle electrodes are partially insulated along an intermediate portion of the shaft so that only that portion in the selected tissue and in the template are conductive. This positions the conductive path through the selected tissue to be treated and isolates overlying tissue from the electrical pulses.

As will be apparent from the foregoing illustration and description, sufficient needle electrodes may be positioned through the connector template in substantially any desired array to cover the necessary area of tissue to which electroporation is to be applied. The needle electrodes may be constructed of any suitable electrically conductive materials. By way of example but not limitation such materials may include platinum, silver, gold, stainless steel and or alloy of these and/or other materials. In certain applications the tissue to be treated lies beneath healthy tissue, the electrodes may preferably be insulated along a portion of the length to isolate the overlying tissue from the pulses. The needle electrodes may also take any suitable form and have any suitable length for the particular application. For example, in an application wherein insertion into or through hard material such as bone is necessary, the needle may be formed with a suitable drilling point such as illustrated in FIG. 2A. Referring to FIG. 2A, a needle electrode 69 is shown formed with a spade type drilling point 69a for drilling through bone and other hard tissue. The point may be formed as a twist drill or in any other suitable drill configuration. The drill point electrode may be rotated by any suitable power means such as a hand drill or a small hand held drill motor.

Figure 3:
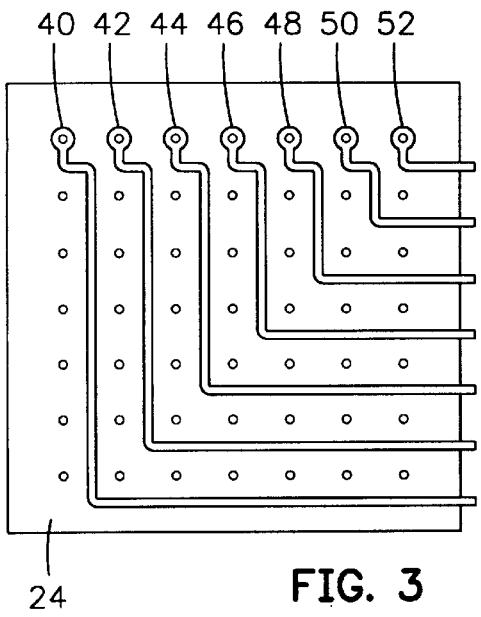
FIG. 3 is a first layer or PC board of the connector of FIG. 1.
Figure 10:
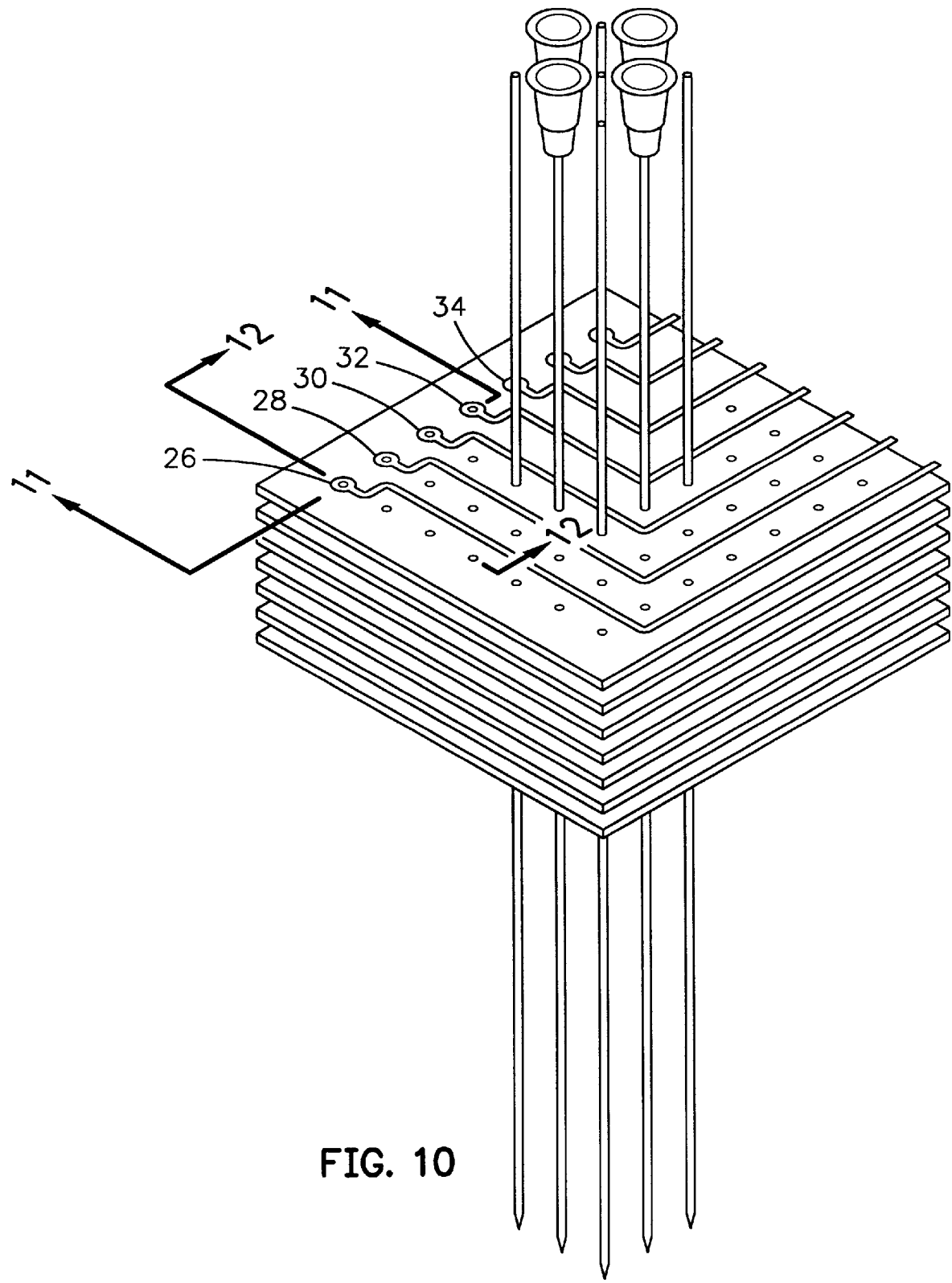
FIG. 10 is a perspective view illustrating the positioning of the layers of FIGS. 3–9 with needles shown in position.

Referring now to FIGS. 3–9, there is illustrated a plurality of printed circuit boards which are stacked together to make up the combined template connector 22. A PC board 24, as shown in FIG. 3, forms the face 24 of the connector template unit. This board, as in each of the boards, has a dimension of about 5 cm$^2$. Due to the small space available for the through holes which include the connectors for the respective electrodes, separate circuits for several of the through holes such as each row of the through holes are put on separate PC boards. Thus, as illustrated in FIGS. 3–9, separate connectors and conductors for each row of the needle electrodes that will be inserted in a through hole are formed on the surface of a separate PC board. These are then stacked in an array, as illustrated, for example, in FIG. 10. It will be appreciated that the connections for the respective holes in the PC boards can be made in any number of arrangements, such as a vertical or horizontal array.

Figure 4:
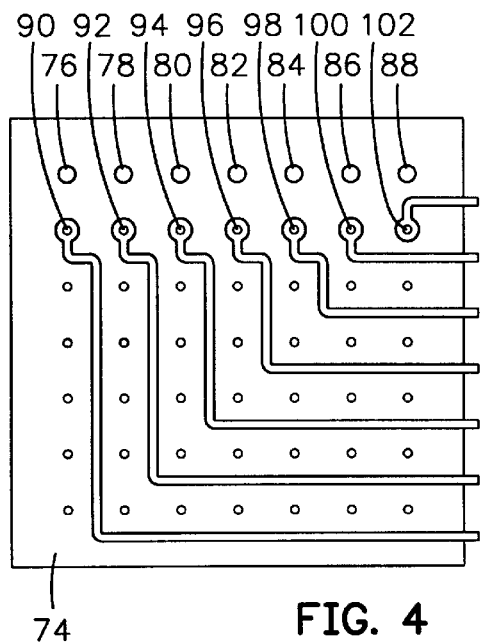
FIG. 4 is a view like FIG. 3 of a second layer of the connector.
Figure 5:
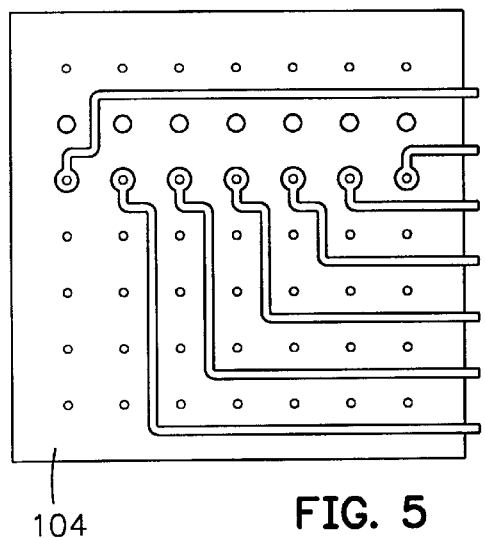
FIG. 5 is a view like FIG. 3 of a third layer of the connector.
Figure 6:
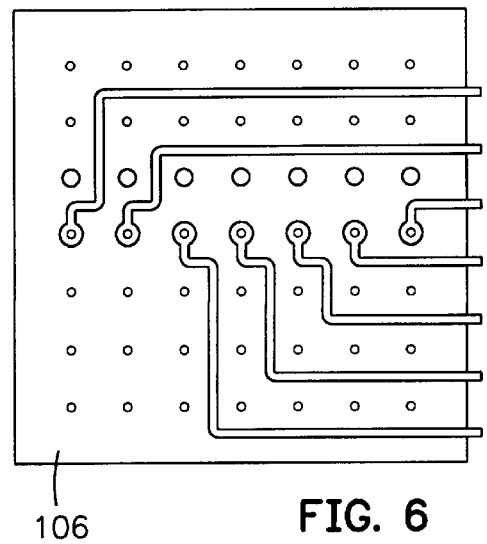
FIG. 6 is a view like FIG. 3 of a fourth layer of the connector.
Figure 7:
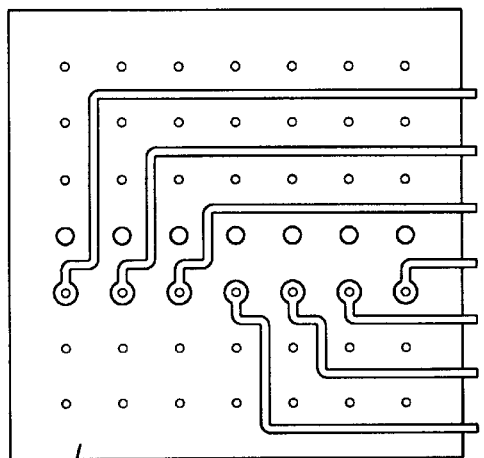
FIG. 7 is a view like FIG. 3 of a fifth layer of the connector.
Figure 8:
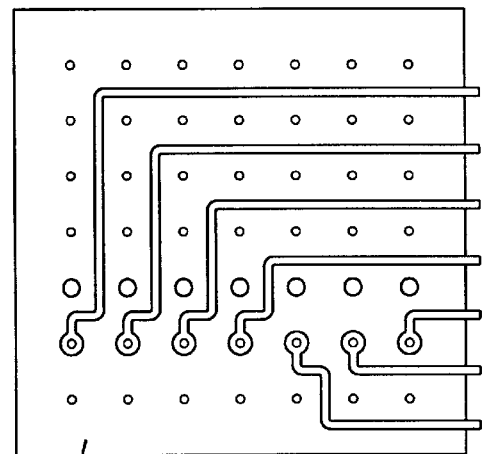
FIG. 8 is a view like FIG. 3 of a sixth layer of the connector.
Figure 9:
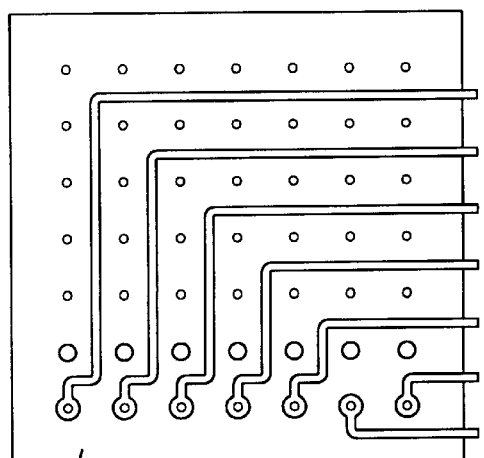
FIG. 9 is a view like FIG. 3 of a seventh layer of the connector.
Figure 11:
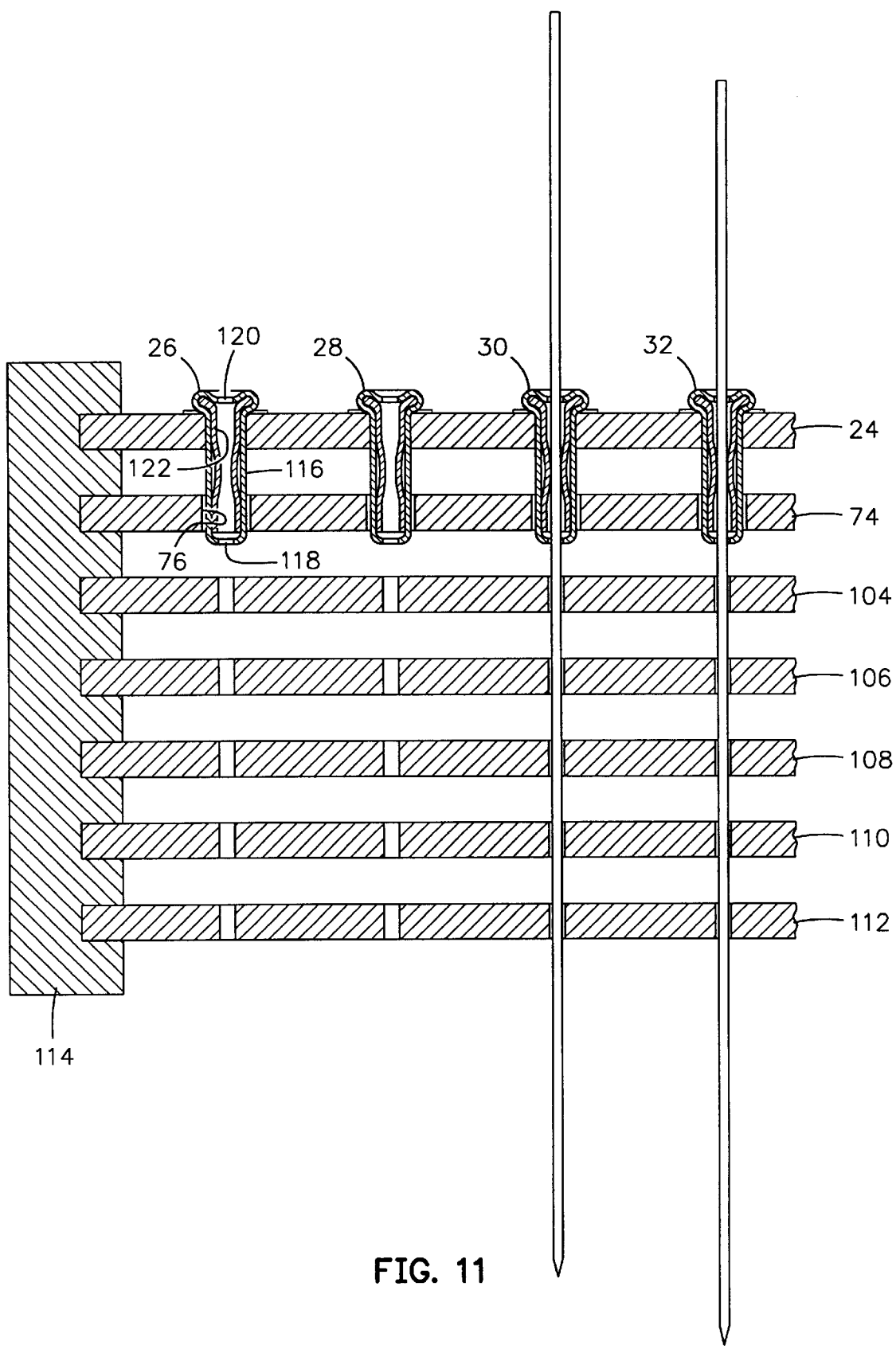
FIG. 11 is a partial sectional view taken along a row of connectors.

Referring now to FIG. 4, it will be seen that a PC board 74, which will be disposed directly below the PC board 24, has a row of enlarged holes 76–88 which are designed to receive the lower end of connectors on the board above, as illustrated in FIG. 11. In addition, this PC board has a row of connectors 90–102 which forms the second row of connecting holes for the needle electrodes of the assembly. These connecting sockets are each connected as in the previous embodiment to separate conductors extending along the surface of the PC board to an edge of the board where they will be connected to the cable 2). Each connector is separately connected through its own conductor into the circuit to the pulse generator where it can be connected in any desirable manner to the generator. For example, each needle can be paired with each adjacent needle in either like polarity or opposed polarity. Thus, the needles can be pulsed in pairs (i.e., two needles of opposed polarity), in multiple pairs (i.e., pair against pair), or in opposed rows (i.e. row against row with odd, even or different numbers of electrodes in opposition).

Referring now to FIG. 11, a sectional view of a portion of the connector assembly is illustrated in section. It shows a plurality of the circuit boards mounted in a frame 114 which supports them in a slightly spaced relationship, as shown. As illustrated, the sockets, such as socket 26, for example, comprises a generally tubular metal shell 116 formed to have an opening 118 at the lower end, and an opening 120 at the upper or inlet end. The shell is formed and crimped around spring contacts 122, which is constricted or bend inward at the center for sliding contact or engagement with a needle. The socket assembly is of a length to extend through bores in the upper PC board 24 through bore 76 in the underlying PC board 74. The socket assemblies are in conductive contact with the printed circuit conductors on the face of the respective board.

Figure 12:
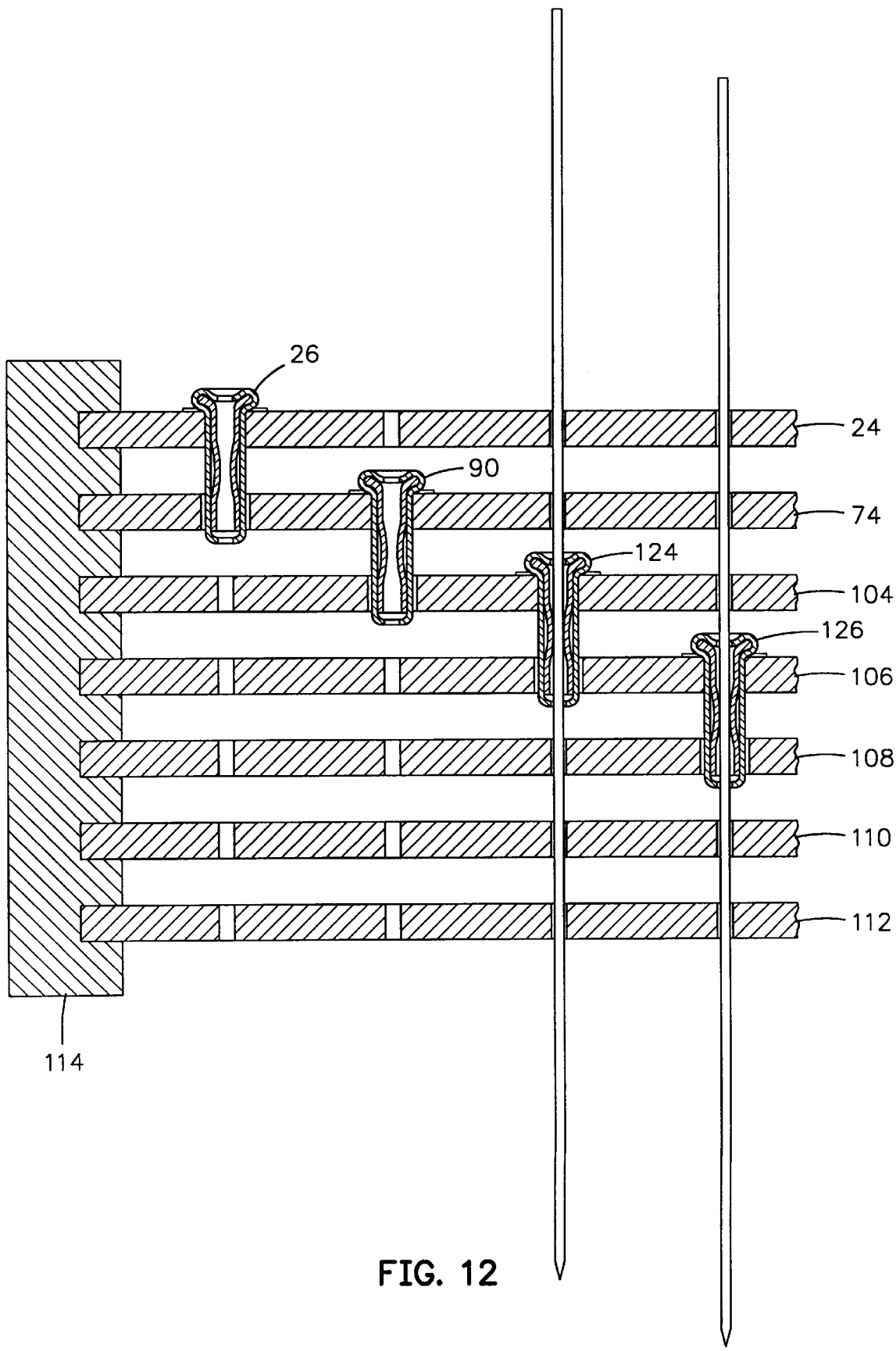
FIG. 12 is a partial sectional view taken across three lines of conductors of the unit.

Referring to FIG. 12, the staggered arrangement of the conductors on the PC boards is illustrated. As illustrated, the second row of conductors or sockets are formed in the PC board 74, which is disposed below the PC board 24. The next lower PC board 104 has a row of conductive sockets, including socket 124 with conductors running along the surface thereof, as previously described. The next row of conductive sockets is on the next lower PC board 106, including a socket 126. Thus, the connectors to the respective electrodes are disposed on different layers within the array of circuit boards. This enables the formation of a combined connector template having very close spacing between the respective conductors, and thereby enable the provision of a high density array, as illustrated.

The above described apparatus of the present invention is shown in use as a prostate cancer electroporation therapy system in FIG. 2 in the illustration. The template is positioned with the plurality of needles inserted into a prostate 130, as illustrated. In exemplary embodiment the template is mounted on a handle or extension 154 of an ultra-sound probe 156 by means of a clamp 136. The ultra-sound probe is inserted into the rectum of the patient and utilized by the physician to visualize the tumor in the prostate. The physician inserts the ultra-sound probe and then inserts the needles into the tumor through the template. Thereafter, chemicals are delivered through a plurality of the needles, which are hollow, into the tumor in the prostate. Thereafter, electrical pulses are delivered to the needles, in a suitable switching scheme, such as described in the above application, or as will be subsequently described. For example, at least one pulse is initiated between two opposing pairs of needles, the pulse is then reversed in polarity, then with 90° change of the needle connection, two more pulses are applied in a first and then a second polarity.

The above described template array can involve up to 49 electrodes, each with a separate connection to the pulse generator. It is desirable in some instances to minimize the number of electrodes which need to be switched or addressed by the generator. In alternate embodiments hereinafter described, the arrangement of the electrodes are in a number of parallel connection so that several zones can be switched simultaneously thereby reducing the number of switching required.

Figure 13A:
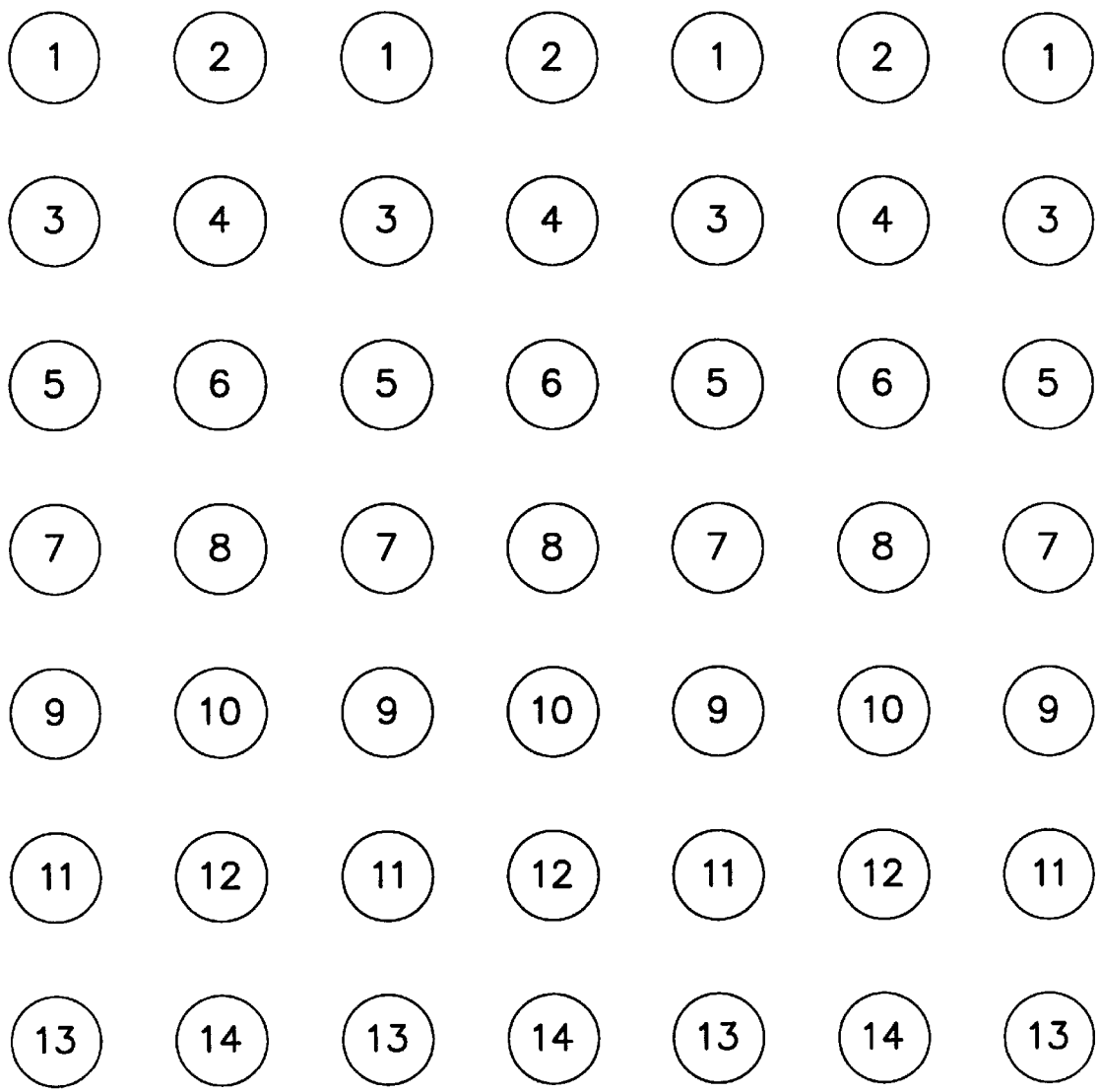
FIG. 13A is a schematic illustration of a needle electrode array of FIG. 1 with an alternate electrode connection mode.

Referring to FIG. 13 A, an array of forty-nine needle electrodes is illustrated wherein all of the electrodes with the same number are connected in parallel. Thus, every other electrodes in each horizontal row is connected in parallel. As can be seen, by switching all electrodes 1 and 2 against needles 3 and 4, then all electrodes 1 and 3 against all electrodes 2 and 4 and then reversing the polarity, only four pulses are needed to cover the entire tissue area between the first row and the second row. Pulses can be similarly applied between all adjacent rows of electrodes. A treatment zone is the area between four electrodes, with the electrodes pulsed in opposed pairs, i.e., a pair of positive against a pair of negative. The preferred pulsing scheme is one pulse between the opposing pairs, second pulse between the same pair in reversed polarity. The switching then rotates 90 degrees to pair the electrodes 90 degrees to the first pair and pulse with a first polarity then with an opposite polarity. This pulsing scheme would be carried out for each row and an adjacent row throughout the entire array of electrodes with 28 pulses. The effectiveness of this opposed pairs approach has been verified.

Figure 14:
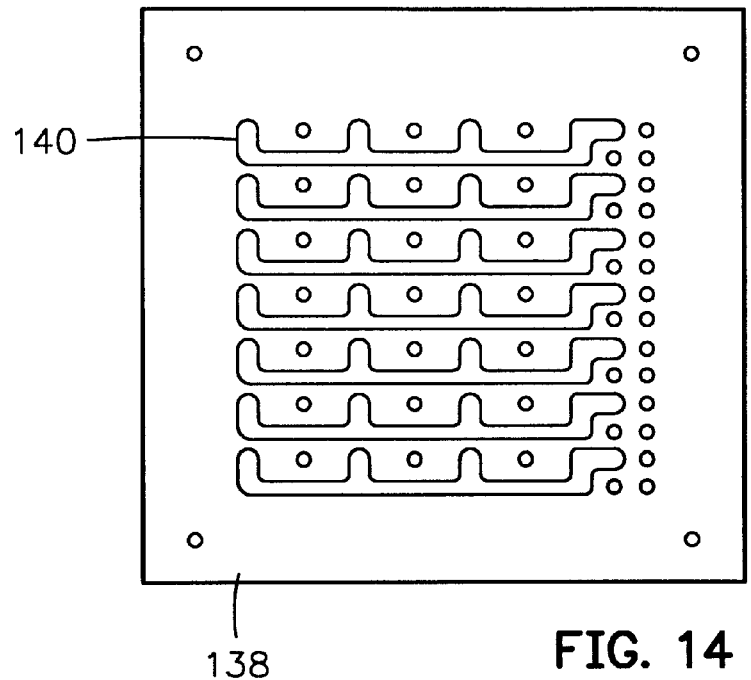
FIG. 14 a plan view of a PC board showing circuit connections for the layout of FIG. 13.
Figure 15:
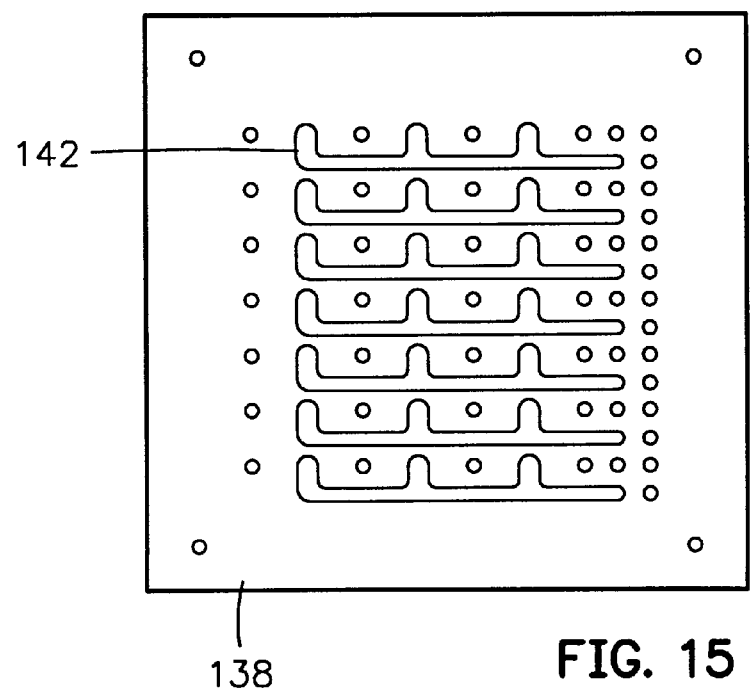
FIG. 15 is a view like FIG. 14 of a second series of connections for the layout of FIG. 13.

This electrode arrangement can be carried out by a two-layer circuit board as illustrated in FIGS. 14 and 15, which requires only 14 connections to the pulse generator. In the illustrated lay-out, all of the same numbers are connected to the same conductor connection in parallel. This entire array can be made up on a two-layer printed circuit board. The principal of switching zones in parallel can be varied further with so many needles in parallel that only four pulses are needed to switch the entire template of 49 needles. Thus, at least multiple, if not all, treatment zones would be simultaneously pulsed.

Figure 13B:
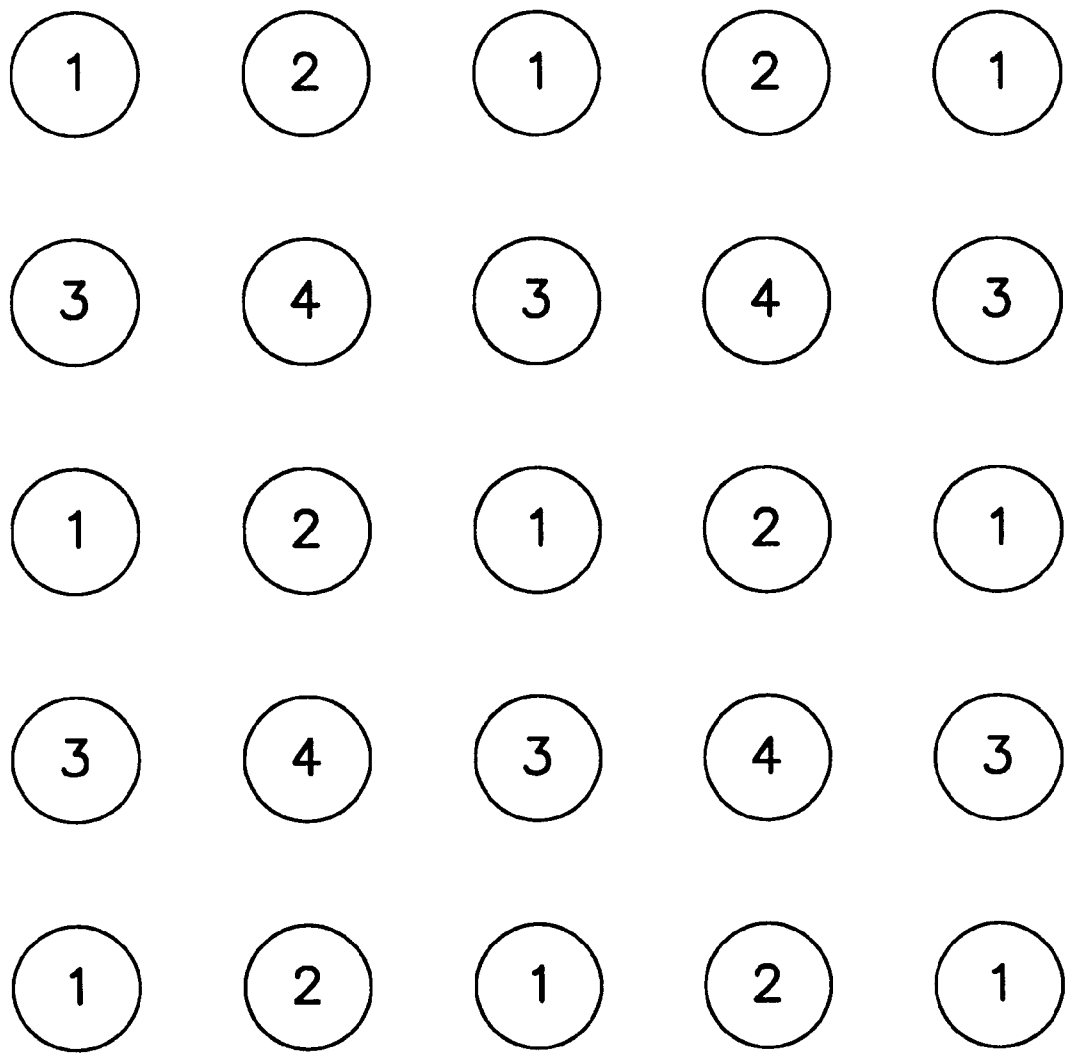
FIG. 13B is a schematic illustration of a an alternate needle electrode array with an alternate electrode connection mode.

Referring to FIG. 13B, an alternative array of twenty-five needle electrodes is illustrated wherein all of the needles with the same number are connected in parallel on the circuit board. Thus, alternate electrodes in both horizontal and vertical rows are connected in parallel. All suitable electrodes 1 and 2 are pulsed against needles 3 and 4 which are connected together in parallel; second pulse is to the same electrodes with reversed polarity; third pulse electrodes 1 connected to electrodes (3 and pulsed against electrodes (2 and 4 connected together; fourth pulse in reverse polarity to this connection. With this connection and pulsing scheme, any large template with any number of electrodes can be pulsed with only four pulses.

This switching scheme and variations thereof can be applied to arrays of any size and substantially any shape. The electrode arrangement and switching scheme of FIGS. 13A can be carried out by a two-layer circuit board as illustrated in FIGS. 14 and 15, which requires only 14 connections to the pulse generator. As illustrated in FIGS. 14 and 15, a multi-layer connecting template 138 showing a conductor 140 connecting four of the needle connecting ports in a first row in parallel. A second layer which may be internal or on the reverse side of the same board is shown in FIG. 15 with a conductor 142 connecting the three remaining of the needle sockets in the first row in parallel. Thus, with this arrangement, seven conductors on each layer can connect all sockets on the entire board in this manner to the pulse generator. The sockets of the circuit board are provided with spring contacts as previously described, which allow the needle electrodes to make sliding contact and to be extended and retracted. This enables them to be easily applied to a design which allows the needles to be extended from and retractable into a holder.

The above described circuit board systems enables any number of different arrays of the needle electrodes, preferably with multiple needles in multiple parallel rows. The needles in each row may be the same or different in number and may be in direct opposition or may be offset. In addition to the various arrays of electrodes, the electrodes may be pulsed in any number of different selectable arrays and sequences, not necessarily limited by the physical array. In its broadest sense, it is preferred that multiple electrodes of one polarity will be pulsed against multiple electrodes of the opposite polarity. The multiple electrodes will be at least pairs and may be even or odd in number or may be the same number in opposition to the same or different number. Several exemplary optional arrays of electrodes are illustrated in the following FIGS. 16–19, each of which may have an advantage in particular applications.

Figure 16:
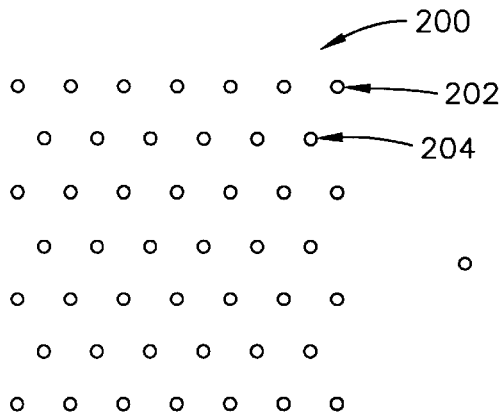
FIG. 16 is a schematic illustration of an alternate embodiment of an electrode array.

Referring to FIG. 16, a generally rectangular array with alternate offset rows of needle electrodes is illustrated and designated generally by the numeral 200. In this array, horizontal rows, such as 202 and 204 are parallel with electrodes in row 204 less in number and offset laterally from electrodes in row 202. It will be seen that vertical rows with alternate offset rows are also formed. Each electrode in each of the inner shorter row is equally spaced from two electrodes in each adjacent row. Pairing multiple electrodes will result in a non-rectangular area of coverage.

Figure 17:
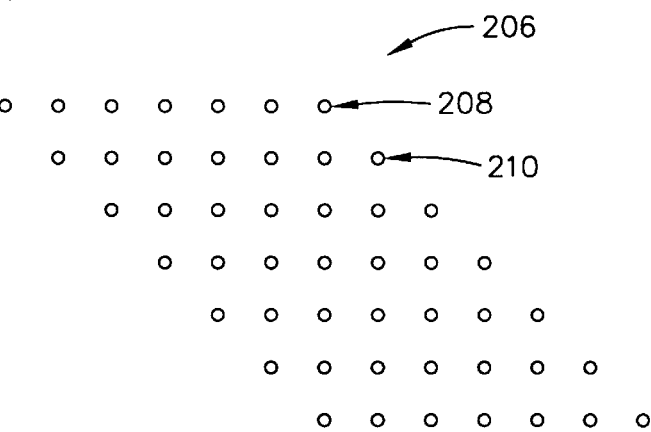
FIG. 17 is a schematic illustration of another embodiment of an electrode array.

Referring to FIG. 17, an electrode array is illustrated wherein each row of electrodes have the same number of electrodes and are laterally offset in one direction one space, and designated generally be the numeral 206. The alternate rows could be offset in alternate directions, rather than in the same direction as illustrated. It will be seen that multiple electrodes are in each row except the first and last vertical rows. All horizontal rows, such as 208 and 210 have the same number of electrodes, and all vertical rows have a different number of electrodes. All vertically inclines rows have the same number with adjacent rows offset one half space. Pairs have same number of electrodes and are laterally offset in one direction one space.

Figure 18:
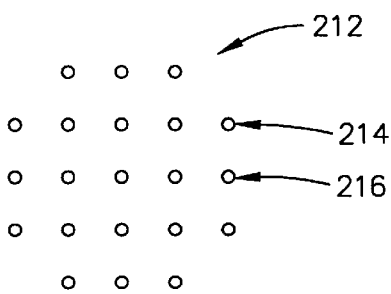
FIG. 18 is a schematic illustration of a further embodiment of an electrode array.

Referring to FIG. 18, a generally rectangular electrode array, designated generally at 212, is illustrated wherein each outermost row of electrodes have the end electrodes missing. The outside rows, such as 214 and 216, have fewer electrodes and are shorter than adjacent inner rows. However, all rows are vertically and horizontally aligned, so that electrodes may be pulsed in multiple pairs and multiple opposed electrodes in adjacent parallel rows.

Figure 19:
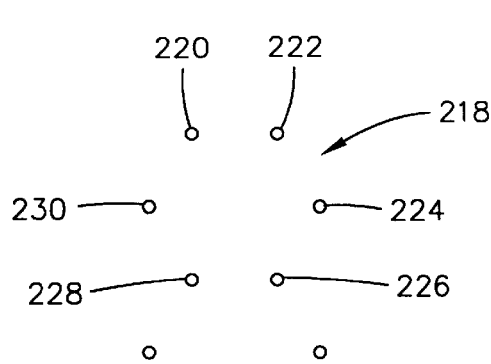
FIG. 19 is a schematic illustration of a still further embodiment of an electrode array.

Referring to FIG. 19, a double circular array of six electrodes is illustrated forming a generally hexagonal electrode array, and designated generally by the numeral 218. This array can comprise a single or multiple hexagonal, with needles 222, 224, 226, 228 and 230 forming one hexagonal. Each hexagon delineates or encircles a treatment area, wherein each electrode may be paired with each adjacent electrode in like polarity and switched in polarity. In this array needles are preferably paired in like polarity against pairs of opposite polarity. Thus, each electrode (such as 220) is paired with adjacent electrode 222 in like polarity and is pulsed against electrodes 226 and 228 which are paired in opposite polarity. The system includes switch means for pairing each electrode with an adjacent electrode in any polarity and switch in polarity progressively around the circle. This array has the advantage of more thoroughly electroporating the selected area tissue, because two pulses from each pair will traverse the area. Opposing pairs of needles are pulsed in sequence around the array in alternate polarity.

Figure 20:
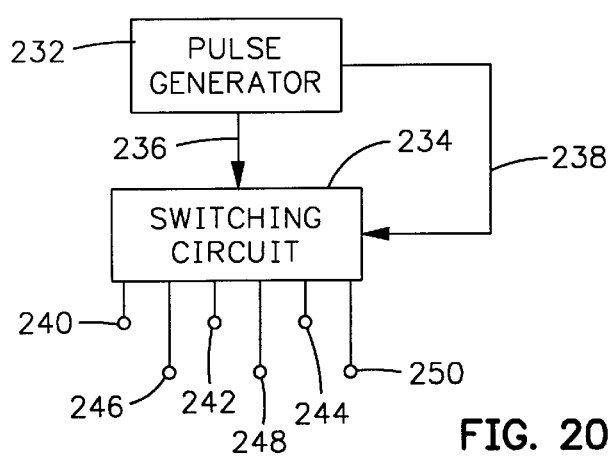
FIG. 20 is a schematic illustration of a system including a pulse generator and switching circuit connected to an electrode array.

The pulses to the electrodes may be applied in any suitable manner with any suitable system such as the system diagrammatically illustrated in FIG. 20. A pulse generator 232 delivers pules 234 via switching circuit 236 to electrodes 240, 242, 244, 246, 248 and 250. The electrodes may be in any selected array. Following each pulse control means associated with the generator switches the switching circuit via a signal 238 causing a switching of the electrodes in polarity and/or pairing. In a preferred arrangement, the switching circuit may separately connect each electrode in either polarity and pair it with each adjacent electrode in like or opposite polarity.

Figure 23:
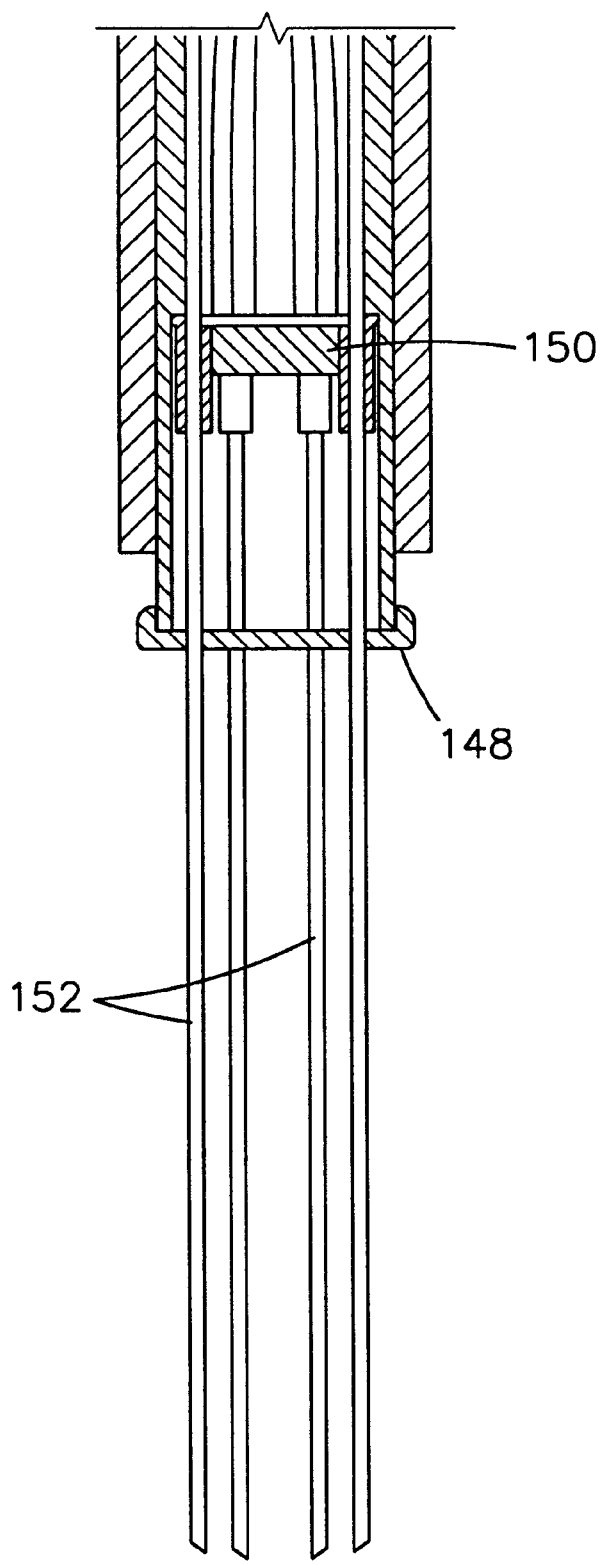
FIG. 23 is an enlarged view showing details of the holder of FIG. 21.

Referring to FIGS. 21–26, an extendable and retractable assembly is illustrated and designated generally by the numeral 144. The assembly comprises an elongated central support member 146 having a head or nose piece 148. A circuit board 150 having a plurality of sliding through-sockets into which needles are mounted on the support member 146 and receive the extending and retracting needles. A plurality of needles 152 are mounted on a tubular sleeve 154 which is mounted on the central support member 146. As the sleeve is moved along the support member, it alternately extends and retracts the needles, as illustrated in FIG. 23. The device is also preferably provided with an indicator or gauge 156 to provide an indication of the length of extension of the needles. In operation, the nose piece 148 is placed against the tissue through which the needles are to extend and the sleeve 154 extended until the needle electrodes extend to the desired depth. As in previous embodiments, one or more of the electrodes may be a hollow needle for the introduction of genes or drugs. A cable 158 connects the needle electrodes of the device to a pulse generator.

Figure 24:
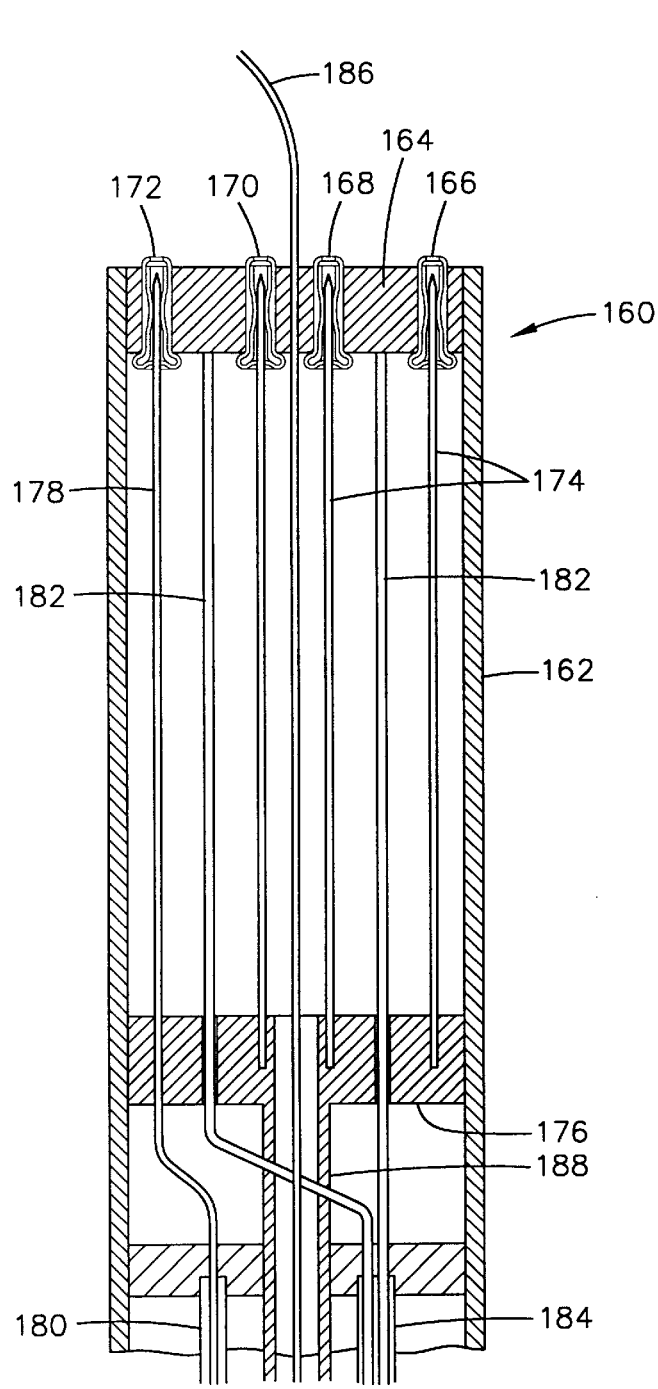
FIG. 24 is a side elevation view in section illustrating an embodiment of the invention like FIG. 21 adapted for a catheter showing the needle electrodes in the retracted position.
Figure 25:
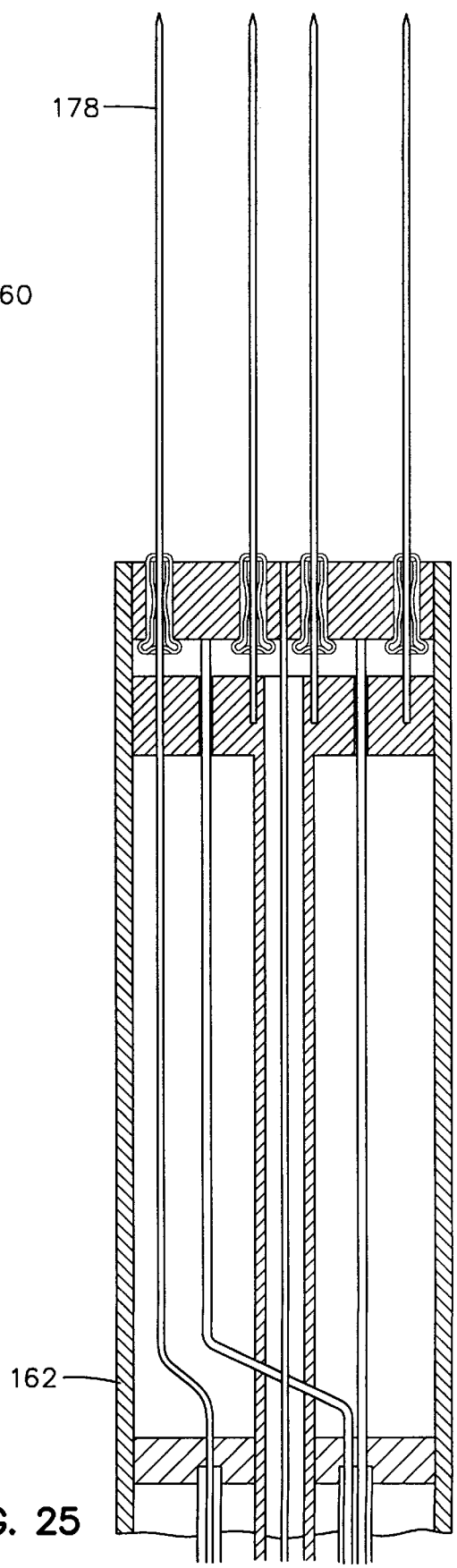
FIG. 25 is a view like FIG. 24 showing the needle electrodes in the extended position.
Figures 26, 27:
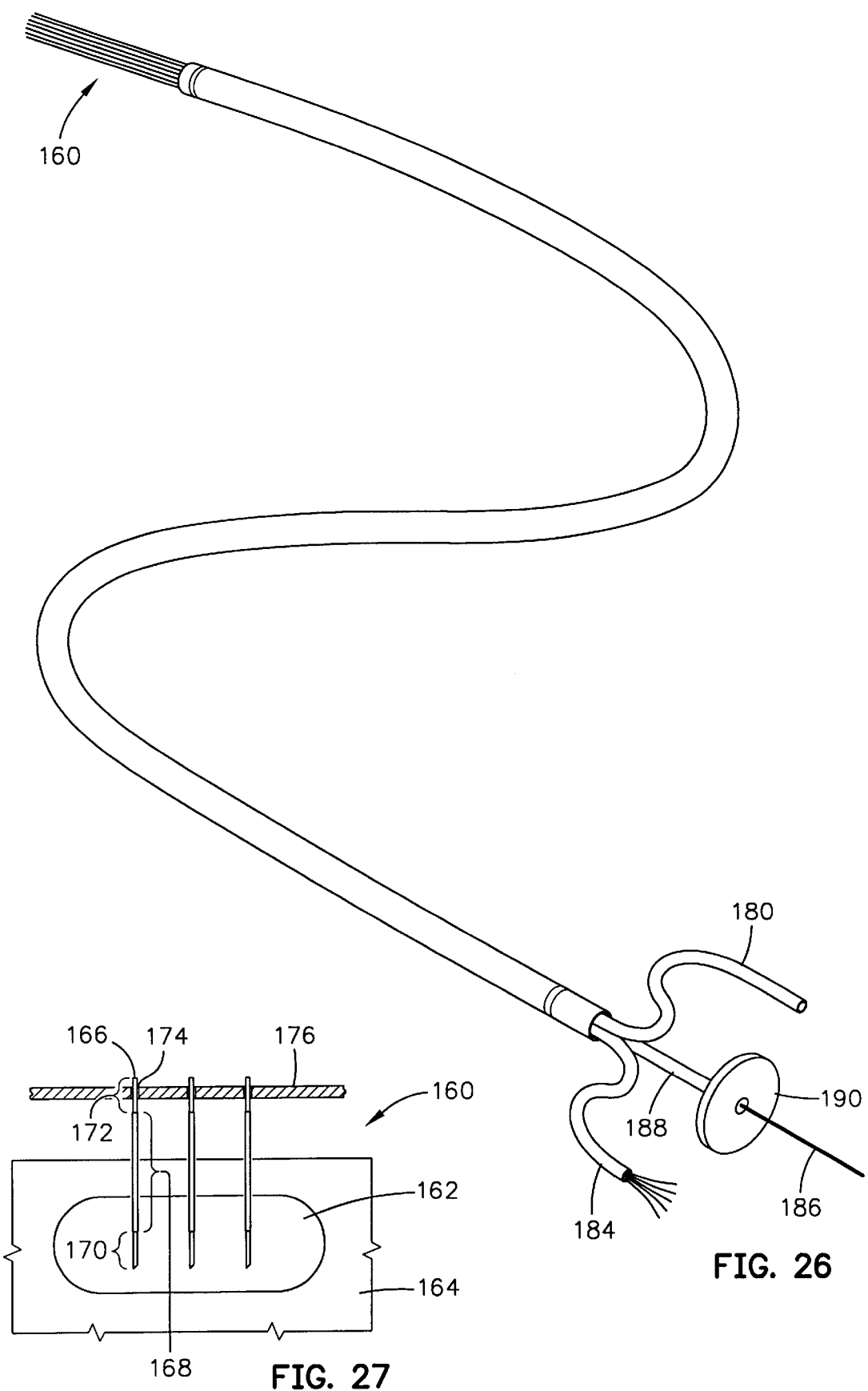
FIG. 26 is a perspective view of a catheter embodying the electrode array of FIG. 24.
FIG. 27 is a side elevation view in section illustrating another embodiment of the invention in use.

The extendable and retractable needles can also be advantageously applied to a catheter. Referring to FIGS. 24–26, a catheter tip assembly is illustrated and designated generally by the numeral 160. In this embodiment, an elongated flexible catheter member 162 is fitted at a distal end with a template 164) having a plurality of through-sockets with sliding connectors 166, 168, 170 and 172. A plurality of solid conductor electrodes 174 are mounted in a moveable actuator plate 176 for movement along the catheter. A hollow needle 178 for the infusion of nucleic acids or drugs is mounted in the moveable support plate 176 and extends through one of the through-sockets and by way of a lumen 180 to a source of drugs or genes not shown. As shown in FIG. 20, the needle electrodes may be extended and retracted from the end of the catheter.

As shown in FIG. 21, the catheter is an elongated flexible member having the needles at one end and various connectors and manipulating means at the other end. The infusion lumen 180 extends to the proximal end of the catheter for connection to a source of genes or drugs, as the case may be. A plurality of electrode wires or conductors 182 extend to and through a electrode wire lumen 184. These extend from the end of the lumen 184 at the proximal end of the catheter for connection to a suitable pulse generator. A guide wire 186 extends from the distal end of the catheter and extends the length thereof by way of a lumen 188). The lumen 188 is connected at one end to the moveable support 176 and includes a disk 190 at the proximal end for use in extending and retracting the needles from the end of the catheter.

FIG. 27 illustrated an area of tissue of the body of a mammal designated generally by the numeral 160 wherein a selected area of tissue such as a tumor or an organ 162 is embodied within tissue 164. A plurality of needle electrodes, only one of which 166 will be described in detail are selected and inserted through the body tissue 164 into the selected tissue 162. The electrodes are provided with an insulating coating along a mid portion 168 thereof. A tip portion 170 is left bare in order to provide conductive contact with tissue 162. An upper portion 172 is also left bare in order to provide conductive contact with conductive strip or contacts in bore 174 in PC board 176. This arrangement enables the electrical pulses bo be applied completely within the selected tissue 162 without disturbing tissue 164. This feature can be embodied into any of the previously discussed embodiments of the apparatus.

The above described systems may employ any number of different arrays of the needle electrodes, preferably with multiple needles in multiple parallel rows. The needles in each row may be the same or different in number and may be in direct opposition or may be offset. In addition to the physical array of electrodes, the electrodes may be pulsed in any number of different selectable arrays and sequences, not necessarily limited by the physical array. In its broadest sense, it is preferred that multiple electrodes of one polarity will be pulsed against multiple electrodes of the opposite polarity. The multiple electrodes will be at least pairs and may be even or odd in number or may be the same number in opposition to the same or different number.

The following examples are intended to illustrate but not limit the invention. While they are typical of those that might be used, other procedures known to those skilled in the art may alternatively be used.

EXAMPLE 1

IN VITRO STUDIES OF ELECTROPORATION THERAPY

PC-3 cells (ATCC CRL-1435, a prostate cancer cell line) were grown in RPMI-1640 supplemented with 15% fetal calf serum (FCS) and 1% L-glutamine in 5% $CO_2$ at 37° C. Cells in the exponential phase of growth were harvested by trypsinization and their viability was determined by trypan blue exclusion. Cell were suspended in culture medium at $2 \times 10^5$ cells/ml and seeded in the wells of a 96-well plate at a final concentration of $4 \times 10^4$ cells per well. Cells were pulsed using appropriate needle array electrodes connected to a square wave pulse generator. The needle array was inserted in the well of the 96 well microplate and pulsed using the following parameters:

| | |
|---|---|
| Voltage: | 0–1000 v |
| Pulse Length: | 99 μsec |
| Number of Pulses: | 6 |

Figure 30:
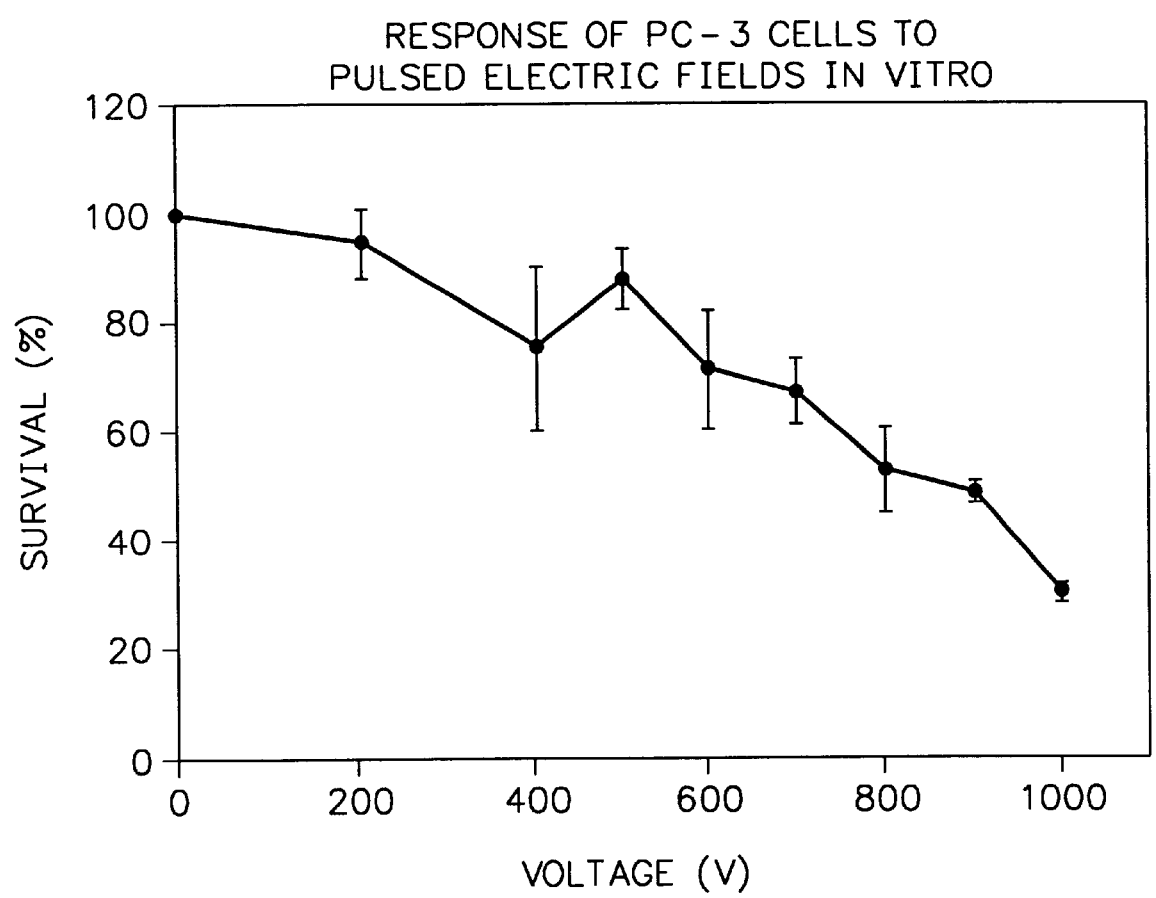
FIG. 30 is a graph of tumor volume of human prostate tumor (PC-3) cells in nude mice. Results are shown for no treatment (●), treatment with bleomycin alone (○), and treatment with bleomycin and electroporation (▼).

A cell survival curve was produced for the different electric fields. The results are shown in FIG. 30. At six pulses of . . . 600 Volts, with a pulse length of . . . μs in a 0.5 cm needle array, 75–80% of the cells survived 20 hours following treatment. Thus, these parameters were selected for the electroporation therapy studies.

Figure 28:
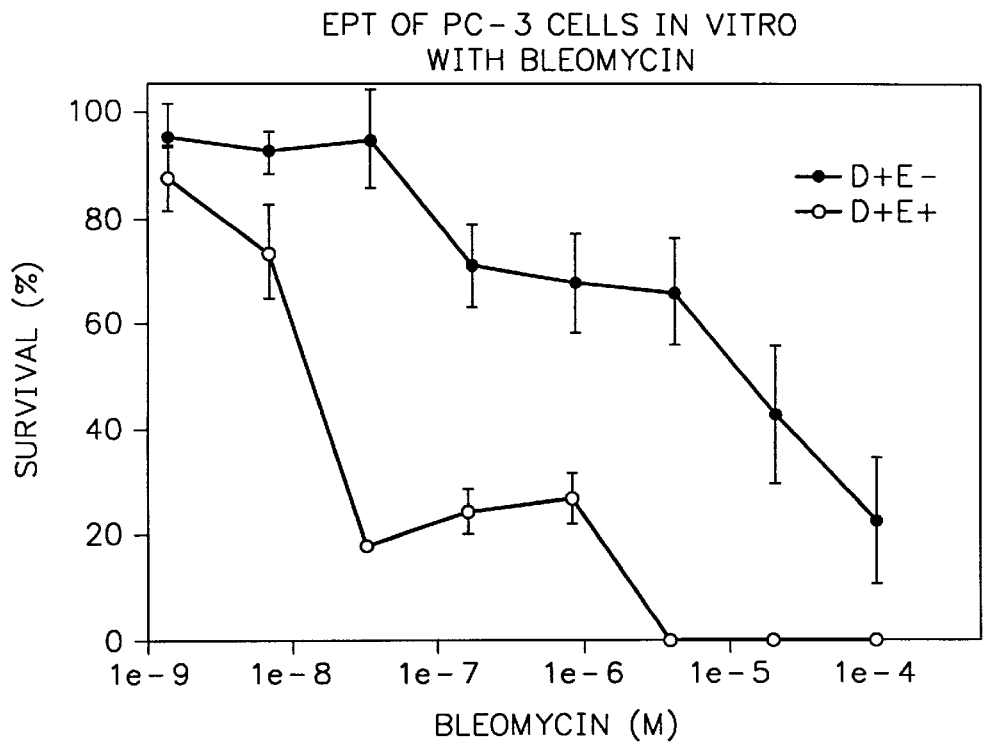
FIG. 28 is a graph of the percentage of PC-3 cells surviving treatment as compared to the voltage (v) applied in vitro.
Figure 29:
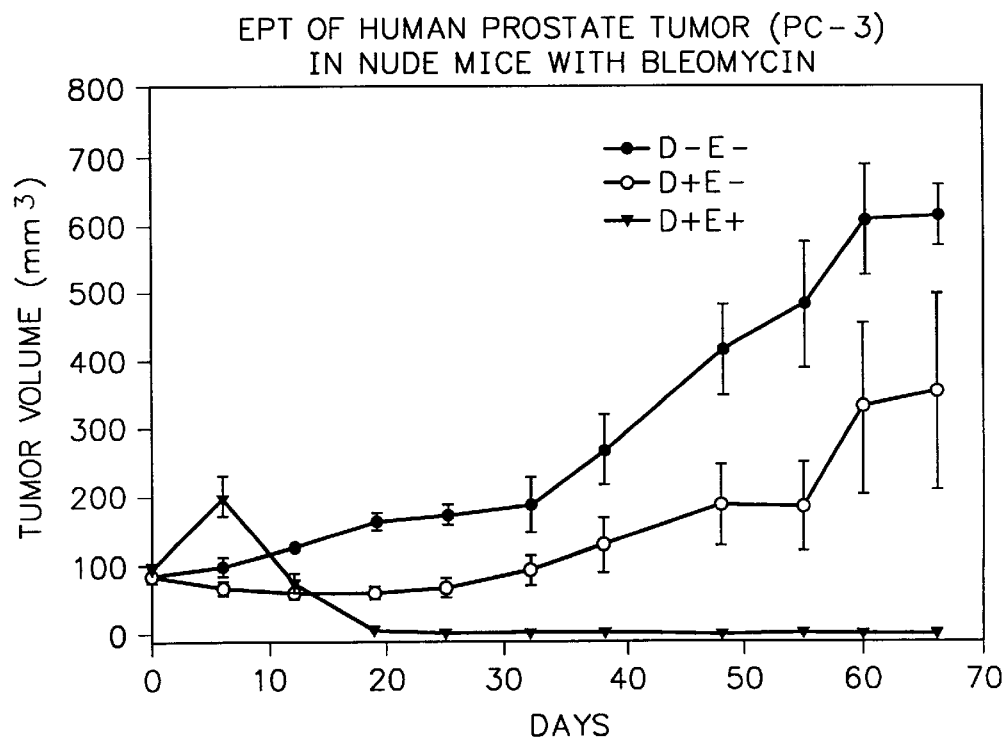
FIG. 29 is a graph of the percentage of PC-3 cells surviving treatment as compared to the bleomycin concentration applied in vitro. Results are shown for cells treated with bleomycin alone (●) and for cell treated with bleomycin and electroporation (○).

Chemotherapeutic agents (Bleomycin, Cisplatin, and Mitomycin C) were dissolved and diluted in phosphate buffered saline (PBS) and added directly to the cell suspensions at final concentrations ranging from $1.3 \times 10^{-9}$ M to $1 \times 10^{-4}$ M. Cell survival in the presence of the chemotherapeutic agents, both with and without the application of the electric field, was determined by XTT cell proliferation assay 20 hours after treatment (Roehm, N. W., Rodgers, G. H., Hatfield, S. M., Glasebrook, A. L., "An Improved Colorimetric Assay for Cell Proliferation and Viability Utilizing the Tetrazolium Salt XTT," *J. Immuol. Methods*, 142:2, 257–265, 1991). The XTT assay is based on a spectrophotometric assay of the metabolic conversion of tetrazolium salts to formazan; living cells convert XTT to formazan, which can be measured spectrophotometrically. A sample survival curve is shown in FIG. 28. Results were expresses as a comparison of the $IC_{50}$ (concentration of drug inhibiting 50% of the cells) of each agent in the presence and absence of electroporation, and are presented in Table 1.

TABLE 1

EFFECT OF TREATMENT OF PC-3 CELLS IN VITRO

| Agent | $IC_{50}$ no electroporation | $IC_{50}$ with electroporation | cytotoxicity enhancement ratio |
|---|---|---|---|
| Bleomycin | $1 \times 10^{-5}$ | $1 \times 10^{-8}$ | 1000 |
| Cisplatin | $5 \times 10^{-5}$ | $1 \times 10^{-5}$ | 5 |
| Mitomycin C | $8 \times 10^{-5}$ | $6 \times 10^{-5}$ | 1.33 |

The cytotoxic effects of chemotherapeutic agents on PC-3 cells were significantly enhanced by combining the agents with electroporation. The highest cytotoxic enhancement was achieved using Bleomycin and electroporation, followed by Cisplatin and Mitomycin C. (# of in vitro samples varied between 6 and 9. No statistics was done, although in diagram, the standard error is shown). Thus electroporation enhances cell susceptibility to the cytotoxic agents Bleomycin and Cisplatin.

EXAMPLE 2

MURINE MODEL SYSTEM

In order to examine the effect of electroporation on the effectiveness of chemotherapeutic agents in vivo, a nude mouse model was utilized. For these experiments, 0.1 ml of a matrigel solution (a serum-free solution consisting of one part matrigel diluted in four parts RPMI-1640) containing $5 \times 10^6$ PC-3 cells was implanted on the flank of nude mice. The tumors were allowed to grow until a tumor volume of $80 \pm 20$ m³. The mice were weighed and randomly divided into six groups as follows:

Group 1: no chemotherapeutic agent, no electroporation

Group 2: 0.5 unit Bleomycin, no electroporation

Group 3: 0.5 units Bleomycin, 4 needle array, 0.65 cm, 942V, $4 \times 100$ μs pulses Group 4: 0.5 units Bleomycin, 6 needle array, 1.00 cm, 1130 V, $6 \times 100$ μs pulses Group 5: 0.5 units Bleomycin, 6 needle array, 0.50 cm, 559 V, $6 \times 100$ μs pulses Group 6: 0.5 units Bleomycin, 4 needle array, 0.87 cm, 1500V, $4 \times 100$ μs pulses In those animals which received Bleomycin, the chemotherapeutic agent (0.5 unit) was dissolved in 0.01 ml saline and injected intratumorally by "fanning." After $10 \pm 1$ minutes, a Genetronics Medpulser™ device was used to pulse the tumors with a set of either 6 or 4-needle array electrodes. All treatments were given as a single set of pulses.

The animals were monitored daily for morality or any sign of disease for 67 days (see FIG. 24, where D=drug treatment (Bleomycin) and e=electroporation). Tumor size was measured and tumor volume calculated using the formula:

$$\text{volume} = \pi/6 \times a \times b \times c$$

wherein a, b, and c are the length, width, and depth of the tumor in mm.

Following the monitoring period, the tumors were harvested and sections were prepared for histological analyses. Animals were classified as having progressive disease (appearance of new lesions not previously identified or having an estimated increase of 25% or more in existent lesion size), a complete response (complete disappearance of all known disease, a partial response (wherein the tumor size decrease 50% or more). Deaths were noted to be due to infighting of mice in the same cage.

TABLE 2

RESULTS OF TREATMENT OF PC-3 CELLS IN NUDE MICE

| Group | Number of Animals | Results |
|---|---|---|
| 1 | 5 | 4 (80%) Progressive disease |
| | | 1 death |
| 2 | 6 | 6 (100%) progressive disease |
| 3 | 7 | 5 (52%) complete response |
| | | 1 (14%) partial response |
| | | 1 (14%) death |
| 4 | 7 | 5 (52%) complete response |
| | | 1 (14%) partial response |
| | | 1 (14%) death |
| 5 | 6 | 5 (83%) complete response |
| | | 1 (17%) partial response |
| 6 | 8 | 5 (63%) complete response |
| | | 1 (12%) partial response |

TABLE 2-continued

RESULTS OF TREATMENT OF PC-3 CELLS IN NUDE MICE

| Group | Number of Animals | Results |
|---|---|---|
| | | 2 (25%) death |

The results indicated that the combination of a chemotherapeutic agent and electroporation is an effective modality for tumor treatment. Both the 4 and the 6 needle arrays were shown to be efficacious.

EXAMPLE 3

EVALUATION OF THE TECHNICAL FEASIBILITY OF INTRAPROSTATIC INJECTION OF BLEOMYCIN

In order to evaluate the technical feasibility of intraprostatic injection of Bleomycin, the following study was performed. A male beagle dog with a prostate size of $\geq 2$ cm in diameter was anesthetized, A midline laparotomy was performed, and the bladder and gut reflected to visualize the prostate gland. Under direct visual guidance, Bleomycin was injected into each of six sextants (base, mid, and apex of both the left and right sides) of the prostate. Four electroporation needles were then inserted transperineally under visual guidance to administer the electroporation cycles. No acute local or adverse reactions to the test compound or electroporation were noted. Small hematomas were evident at the injection site, which persisted for the duration of the study. During the electroporation pulses, muscular contractions were observed. The ECG was recorded during each of the electroporation pulse sequences. The first two sequences were conducted with the needles inserted into the prostate, through the perineum. Four additional sequences were recorded with the needles inserted directly into the muscles of the left hindlimb. Each of the pulse sequences produced stimulation artifacts on the recording of the ECG. However, it was still apparent from the ECG recordings that there was no effect on the electrical rhythm of the heart, as the timing of the QRS complexes appeared not to differ during the train of the electroporation pulses, and no clinical disturbances of the cardiac rhythm were observed.

One hour after electroporation, the animal was euthanized using Beuthanasia cocktail, and the prostate, perineum, and surrounding tissues were examined for gross lesions, in situ. Gross examination of the prostate, perineum, and surrounding tissues revealed no findings except for the hematomas on the prostate surface. The prostate was then excised and processed for histological evaluation. The significant tissue findings noted in the prostate gland included hemorrhage, edema, and necrosis, which were mild in severity and multifocal in distribution pattern. Necrosis occurred in the epithelial cells in the glandular portion of the prostate. No necrosis of the supporting stroma was observed. The study demonstrated that the treatment protocol can be utilized to induce necrosis of the prostate.

EXAMPLE 4

CANINE MODEL SYSTEM OF INTRAPROSTATIC BLEOMYCIN AND ELECTROPORATION

In order to investigate the toxicity and side effects of combined Bleomycin and electroporation in the prostate, a canine model was evaluated. Male beagle dogs with a prostate size of $\geq 2$ cm in diameter are utilized. The following methods are used:

Group 1A, D–E+ (d=drug, E=electric field, +/−=presence or absence, respectively)

Under general anesthesia, an open laparotomy is performed to expose the prostate. Electroporation needles are inserted transperitonealy into the prostate form the base to the apex. of the prostatic capsule. These are inserted using the square array templated guides (0.5 cm base length) and transrectal ultrasound (TRUS) ultrasound. The needle placement and spacing are confirmed with fluoroscopy. Saline (0.25 ml/cm3) is injected transperitonealy into the prostate. The injection is delivered to the base, mid and apex portions of the prostate lobe using the TRUS guidance. Succinylcholine was given, prior to electroporation, 1 mg/kg, i.v. An EP pulse is applied according to the following treatment parameters:

Experiment #1: EPT cycle (658 V) with a four needle array (1×treatment area). Sacrifice at 48 hours post-electroporation.

Experiment #2: 3 EPT cycles (658 V) with a four needle array (1×treatment area). Sacrifice at 48 hours post-electroporation.

Electrode position is monitored by TRUS image before, during, and after electroporation. EKG is monitored before, during and after electroporation. The toxicity is monitored by examining urination (void, hematuria) at 0, 24, and 48 hours post electroporation. Erection (rectal palpitation) is monitored at 0, 24, and 48 hours post electroporation. The blood chemistry profile (indicating kidney and liver function) is monitored at 0, 24, and 48 hours post electroporation. Both gross pathological exam and histopathological analyses are performed. Specifically, the prostate, testes, urethra, lung, rectum, kidney, bladder and caudi equina are examined.

Group 1B, D–E+

Under general anesthesia, an open laparotomy is performed to expose the prostate. Electroporation needles are inserted transperitineally into the prostate from the base to the apex of the prostatic capsule. These are inserted using the square array templated guides (0.5 cm base length) and transrectal ultrasound (TRUS) ultrasound. The needle placement and spacing are confirmed with fluoroscopy. Saline (0.25 ml/cm3) is injected transperitonealy into the prostate. The injection is delivered to the base, mid and apex portions of the prostate lobe using the TRUS guidance. Succinylcholine was given, prior to electroporation, 1 mg/kg, i.v. An EP pulse is applied according to the following treatment parameters:

Experiment #3: 3 EPT cycles (658 V) with a four needle array (1×treatment area). Sacrifice at 28 days post-electroporation.

Electrode position is monitored by TRUS image before, during, and after electroporation. EKG is monitored before, during and after electroporation. The toxicity is monitored by examining urination (void, hematuria) at days 0, 2, 2, 7, 14, and 28 post electroporation. Erection (rectal palpitation) is monitored at days 0, 2, 2, 7, 14, and 28 post electroporation. The blood chemistry profile (indicating kidney and liver function) is monitored at days 0, 2, 2, 7, 14, and 28 post electroporation. Both gross pathological exam and histopathological analyses are performed. Specifically, the prostate, testes, urethra, lung, rectum, kidney, bladder and caudi equina are examined.

Group IIA: D+E+

Under general anesthesia, an open laparotomy is performed to expose the prostate. Electroporation needles are inserted transperitineally into the prostate from the base to the apex of the prostatic capsule. These are inserted using the square array templated guides (0.5 cm base length) and transrectal ultrasound (TRUS) ultrasound. The needle placement and spacing are confirmed with fluoroscopy. Bleomycin (4 U/ml) is injected tranperitoneally into the prostate at 0.25 ml/cm$^3$ prostate volume (1 U/cm$^3$ prostate volume) using TRUS guidance. Succinylcholine was given, prior to electroporation, 1 mg/kg, i.v. An EP pulse is applied according to the following treatment parameters:

Experiment #4: EPT cycle (658 V) with a four needle array (1×treatment area). Sacrifice at 48 hours post-electroporation.

5: 3 EPT cycles (658 V) with a four needle array (1×treatment area). Sacrifice at 48 hours post-electroporation.

Drug injection and electrode position are monitored by TRUS image before, during, and after electroporation. EKG is monitored before, during and after electroporation. The toxicity is monitored by examining urination (void, hematuria) at 0, 24, and 48 hours post electroporation. Erection (rectal palpitation) is monitored at 0, 24, and 48 hours post electroporation. The blood chemistry profile (indicating kidney and liver function) is monitored at 0, 24, and 48 hours post electroporation. Both gross pathological exam and histopathological analyses are performed. Specifically, the prostate, testes, urethra, lung, rectum, kidney, bladder and caudi equina are examined.

Bleomycin pharmacokinetics are also evaluated. Blood levels are determined at time 0, end of injection and 10, 20, 30, 60 120 minutes post electroporation. The blood level of Bleomycin is further determined and 12, 24, 36, and 48 hours post electroporation.

Group IIB, D+E+

Under general anesthesia, an open laparotomy is performed to expose the prostate. Electroporation needles are inserted transperitineally into the prostate from the base to the apex of the prostatic capsule. These are inserted using the square array templated guides (0.5 cm base length) and transrectal ultrasound (TRUS) ultrasound. The needle placement and spacing are confirmed with fluoroscopy. Bleomycin (4 U/ml) is injected tranperitoneally into the prostate at 0.25 ml/cm$^3$ prostate volume (1 U/cm$^3$ prostate volume) using TRUS guidance. Succinylcholine was given, prior to electroporation, 1 mg/kg, i.v. An EP pulse is applied according to the following treatment parameters:

Experiment #6: 3 EPT cycles (658 V) with a four needle array (1×treatment area). Sacrifice at 28 days post-electroporation.

Drug injection and electrode position is monitored by TRUS image before, during, and after electroporation. EKG is monitored before, during and after electroporation. The toxicity is monitored by examining urination (void, hematuria) at days 0, 2, 2, 7, 14, and 28 post electroporation. Erection (rectal palpitation) is monitored at days 0, 2, 2, 7, 14, and 28 post electroporation. The blood chemistry profile (indicating kidney and liver function) is monitored at days 0, 2, 2, 7, 14, and 28 post electroporation. Both gross pathological exam and histopathological analyses are performed. Specifically, the prostate, testes, urethra, lung, rectum, kidney, bladder and caudi equina are examined.

Bleomycin pharmacokinetics are also evaluated. Blood levels are determined at time 0, end of injection and 10, 20, 30, 60 120 minutes post electroporation. The blood level of Bleomycin is further determined and 12, 24, 36, and 48 hours and 7, 14, and 28 days post electroporation.

Group IIIA, D+E−

Under general anesthesia, an open laparotomy is performed to expose the prostate. Bleomycin (4 U/ml) is injected tranperitonealy into the base, mid, and apex portions of the prostate lobe at 0.25 ml/cm$^3$ prostate volume (1 U/cm$^3$ prostate volume) using TRUS guidance. Succinylcholine was given, prior to electroporation, 1 mg/kg, i.v. The animal (s) are sacrificed 48 hours after Bleomycin treatment.

Drug injection is monitored by TRUS image before, during, and after electroporation. EKG is monitored before, during and after electroporation. The toxicity is monitored by examining urination (void, hematuria) at 0, 24, and 48 hours post electroporation. Erection (rectal palpitation) is monitored at 0, 24, and 48 hours post electroporation. The blood chemistry profile (indicating kidney and liver function) is monitored at 0, 24, and 48 hours post electroporation. Both gross pathological exam and histopathological analyses are performed. Specifically, the prostate, testes, urethra, lung, rectum, kidney, bladder and caudi equina are examined.

Bleomycin pharmacokinetics are also evaluated. Blood levels are determined at time 0, end of injection and 10, 20, 30, 60 120 minutes post electroporation. The blood level of Bleomycin is further determined and 12, 24, 36, and 48 hours post electroporation.

Group IIIB, D+E−

Under general anesthesia, an open laparotomy is performed to expose the prostate. Bleomycin (4 U/ml) is injected tranperitonealy into the base, mid and apex portions of the prostate lobe at 0.25 ml/cm$^3$ prostate volume (1 U/cm$^3$ prostate volume) using TRUS guidance. Succinyl choline is then injected [PLEASE PROVIDE DOSAGE]. The animal (s) is sacrificed after 28 days.

Drug injection is monitored by TRUS image before, during, and after electroporation. EKG is monitored before, during and after electroporation. The toxicity is monitored by examining urination (void, hematuria) at days 0, 2, 2, 7, 14, and 28 post electroporation. Erection (rectal palpitation) is monitored at days 0, 2, 2, 7, 14, and 28 post electroporation. The blood chemistry profile (indicating kidney and liver function) is monitored at days 0, 2, 2, 7, 14, and 28 post electroporation. Both gross pathological exam and histopathological analyses are performed. Specifically, the prostate, testes, urethra, lung, rectum, kidney, bladder and caudi equina are examined.

Bleomycin pharmacokinetics are also evaluated. Blood levels are determined at time 0, end of injection and 10, 20, 30, 60 120 minutes post electroporation. The blood level of Bleomycin is further determined and 12, 24, 36, and 48 hours and 7, 14, and 28 days post electroporation.

Although the invention has been described with reference to the presently preferred embodiment, it should be understood that various modifications can be made without departing from the spirit of the invention. Accordingly, the invention is limited only by the following claims.

What is claimed is:

1. A method for the introduction of an agent to a neoplastic cell for damaging the cell, comprising:

(a) contacting said cell with an electrode template apparatus comprising a primary support member having opposite surfaces;

a plurality of bores arranged in rows and extending through said support member and through said opposite surfaces;

a plurality of conductors on said support member separately connected to at least one of said plurality of bores;

a plurality of needle electrodes mounted in said plurality of bores so that each conductor is connected to at least one electrode;

means for connecting said conductors to a power supply;

(b) contacting said cell with said agent either prior to, simultaneously with or after step (a); and (c) applying an electric field to said cell by utilizing said electrode template apparatus to apply an electric field to at least two pairs of said needle electrodes simultaneously, sufficient to cause electroporation, thereby introducing said agent to said cell.

2. The method of claim 1, wherein said contacting is in vivo.

3. The method of claim 1, wherein the cell is selected from the group consisting of a pancreas, a larynx, a pharynx, a lip, a throat, a lung, a kidney, a muscle, a breast, a colon, a uterus, a prostate, a thymus, a testis, a skin, and an ovary cell.

4. The method of claim 3, wherein said cell is a prostate tumor cell.

5. The method of claim 1, wherein said cell is a mammalian cell.

6. The method of claim 5, wherein said cell is a human cell.

7. The method of claim 1, wherein said plurality of electrodes is selected from the group consisting of a four needle array of electrodes and a six needle array of electrodes.

8. The method of claim 1, wherein the electric field is from about 50 V/cm to 1500 V/cm.

9. The method of claim 1 wherein the electric field is applied as from about 1 to 10 electrical pulses.

10. The method of claim 9, wherein the electrical pulse is from about 5 $\mu$sec to 50 msec in duration.

11. The method of claim 9, wherein the electrical pulse is selected from the group consisting of a square wave pulse, an exponential wave pulse, a unipolar oscillating wave form of limited duration, an a bipolar oscillating wave form of limited duration.

12. The method of claim 11, wherein said electrical pulse is comprised of a square wave pulse.

13. The method of claim 1, wherein said agent is a selected from the group consisting of a nucleic acid, a polypeptide, and a chemotherapeutic agent.

14. The method of claim 13, wherein said chemotherapeutic agent is selected from the group consisting of Bleomycin, Cystplatin, and Mitomycin C.

15. The method of claim 1, further comprising applying a cytokine to said cell.

16. A method for the introduction of an agent to a tissue for damaging a cell in the tissue, comprising:

(a) contacting said tissue with an electrode template apparatus, comprising a primary support member having opposite parallel surfaces;
a plurality of bores arranged in rows and extending through said support member and through said opposite surfaces;
a plurality of conductors on said support member separately connected to at least one of said plurality of bores;
a plurality of needle electrodes mounted in said plurality of bores so that each conductor is connected to at least one electrode, at least one of said needle electrodes having a tubular configuration for injection of said agent into said tissue; and
means for connecting said conductors to a power supply; and (b) contacting said tissue with said agent either prior to, simultaneously with or after (a); and (c) applying a pulse of high amplitude electric signals to at least two pairs of electrodes simultaneously, sufficient to cause electroporation of said cell with said agent.

17. The method of claim 16, wherein said contacting is in vivo.

18. The method of claim 16, wherein said cell is a neoplastic cell.

19. The method of claim 16, wherein the tissue is a mammalian tissue.

20. The method of claim 19, wherein the tissue is a human tissue.

21. The method of claim 16, wherein said tissue is selected from the group consisting of pancreas, larynx, pharynx, lip, throat, lung, kidney, muscle, breast, colon, uterus, prostate, thymus, testis, skin, and ovary.

22. The method of claim 21, wherein said tissue is a prostate.

23. The method of claim 16, wherein said plurality of needle electrodes is selected from the group consisting of a four needle array of electrodes and a six needle array of electrodes.

24. The method of claim 16, wherein said pulse of high amplitude electric signals is from about 50 V/cm to 1500 V/cm.

25. The method of claim 24, wherein the pulse of high amplitude electric signals is applied as from about 1 to 10 electrical pulses.

26. The method of claim 24, wherein the pulse of high amplitude electric signals is from about 5 $\mu$sec to 50 msec in duration.

27. The method of claim 24, wherein the pulse of high amplitude electric signals is selected from the group consisting of a square wave pulse, an exponential wave pulse, a unipolar oscillating wave form of limited duration, an a bipolar oscillating wave form of limited duration.

28. The method of claim 27, wherein said electrical pulse is comprised of a square wave pulse.

29. The method of claim 16, wherein said agent is a selected from the group consisting of a nucleic acid, a polypeptide and a chemotherapeutic agent.

30. The method of claim 29, wherein said chemotherapeutic agent is selected from the group consisting of Bleomycin, Cystplatin, and Mitomycin C.

* * * * *

UNITED STATES PATENT AND TRADEMARK OFFICE
CERTIFICATE OF CORRECTION

PATENT NO. : 6,120,493
DATED : September 19, 2000
INVENTOR(S) : Gunter A. Hofmann It is certified that error appears in the above-indentified patent and that said Letters Patent is hereby corrected as shown below:

In claim 10, line, 1 please delete the word "Tsec" and replace with --µsec--.

In claim 11, line 3, please delete the word "an" before a bipolar.

In claim 14, line 2, please delete the word Cysplatin and replace with --Cisplatin--.

In claim 26, line 2, delete the word "Tsec" and replace with --µsec--.

In claim 27, line 3, please delete the word "an" before a bipolar.

In claim 29, line 1, please delete the word "a" before the word selected.

In claim 30, line 2, please delete the word Cysplatin and replace with --Cisplatin--.

Signed and Sealed this

Fifteenth Day of May, 2001

NICHOLAS P. GODICI

*Attest:*

*Attesting Officer*

*Acting Director of the United States Patent and Trademark Office*